(12) United States Patent
Silverman et al.

(10) Patent No.: US 7,367,941 B2
(45) Date of Patent: May 6, 2008

(54) DETECTION AND CHARACTERIZATION OF CHOLINERGIC OSCILLATORY CONTROL IN PERIPHERAL MICROVASCULATURE

(75) Inventors: David G. Silverman, West Redding, CT (US); Robert G. Stout, Madison, CT (US)

(73) Assignee: Yale University, New Haven, CT (US)

( * ) Notice: Subject to any disclaimer, the term of this patent is extended or adjusted under 35 U.S.C. 154(b) by 499 days.

(21) Appl. No.: 10/437,452

(22) Filed: May 14, 2003

(65) Prior Publication Data
US 2003/0233048 A1    Dec. 18, 2003

Related U.S. Application Data

(63) Continuation-in-part of application No. PCT/US01/43644, filed on Nov. 14, 2001.

(60) Provisional application No. 60/248,009, filed on Nov. 14, 2000.

(51) Int. Cl.
*A61B 5/00* (2006.01)
*A61B 5/02* (2006.01)

(52) U.S. Cl. .................... 600/300; 600/481; 600/500; 600/504

(58) Field of Classification Search .................. None
See application file for complete search history.

(56) References Cited

U.S. PATENT DOCUMENTS

| | | | | |
|---|---|---|---|---|
| 5,291,400 | A * | 3/1994 | Gilham | 600/509 |
| 5,299,119 | A | 3/1994 | Kraf et al. | 364/413.06 |
| 5,755,671 | A * | 5/1998 | Albrecht et al. | 600/516 |
| 5,830,149 | A | 11/1998 | Inukai et al. | 600/481 |
| 5,941,837 | A | 8/1999 | Amano et al. | 600/595 |
| 6,212,427 | B1 * | 4/2001 | Hoover | 600/515 |
| 6,331,162 | B1 | 12/2001 | Mitchell | 600/485 |
| 6,358,201 | B1 * | 3/2002 | Childre et al. | 600/300 |
| 6,416,473 | B1 | 7/2002 | Risk et al. | 600/300 |

\* cited by examiner

*Primary Examiner*—Robert L. Nasser, Jr.
*Assistant Examiner*—Patricia Mallari
(74) *Attorney, Agent, or Firm*—Cooley Godward Kronish LLP

(57) ABSTRACT

The present invention is an apparatus and method for assessing the condition of a subject by measuring and characterizing one or more oscillatory activities of the subject. The oscillatory activities are under the control of the autonomic nervous system and characterizing the activities provides information related to the status of the autonomic nervous system.

28 Claims, 29 Drawing Sheets

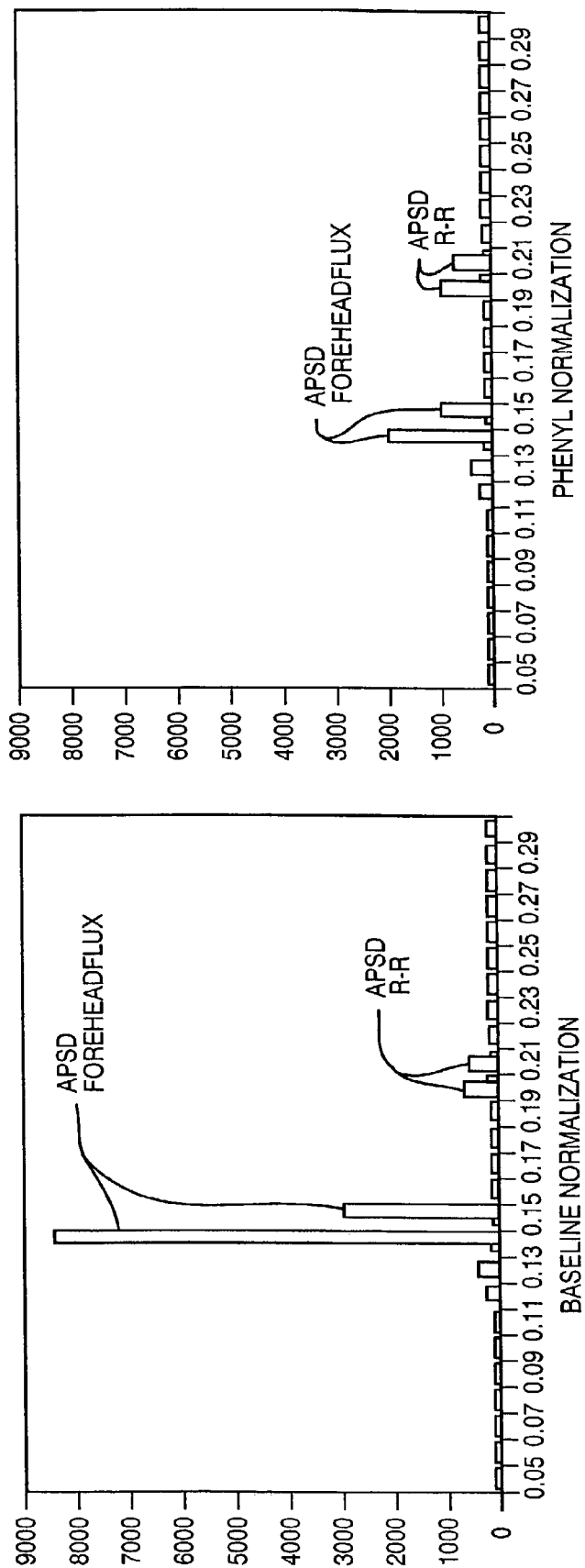

| R-R | BASELINE (BL) | PHENYLEPHRINE | PHENYLEPHRINE + ATROPINE |
|---|---|---|---|
| pNN50(%) | 32.1 (7.3) | 50.8 (8.3) | 0.9 (0.6) |
| pBB5%(%) | 39.2 (6.7 | 50.1 (7.8) | 1.8 (1.2) |
| pBB10%(%) | 10.0 (3.3) | 20.7 (5.1) | .50 (.50) |
| SD (mec) | 60.9 (6.2) | 100.4 (15.2) | 23.9 (6.8) |
| RMSSD (msec) | 51.5 (7.1) | 92.4 (13.3) | 17.2 (8.7) |
| SD/median | 0.069 (.007) | 0.095 (.01) | 0.034 (.01) |
| RMSSD/median | 0.058 (.007) | 0.087 (.01) | 0.027 (.02) |
| Beat-Beat % Change | 4.3 (0.6) | 5.6 (0.7) | 0.9 (0.2) |

| FOREHEAD FLUX (MEAN) | BASELINE (BL) | PHENYLEPHRINE | PHENYLEPHRINE + ATROPINE |
|---|---|---|---|
| PNN50(%) | --- | --- | --- |
| PBB5%(%) | 42.1 (6.4) | 75.1 (3.5) | 44.9 (8.4) |
| PBB10%(%) | 14.9 (7.0) | 49.5 (6.5) | 19.8 (7.8) |
| SD (volts) | 0.22 (.05) | 0.39 (.09) | .20 (.03) |
| RMSSD (volts) | 0.16 (7.1) | 0.34 (.08) | 0.14 (.03) |
| SD/median | 0.105 (.02) | 0.18 (.02) | 0.12 (.02) |
| RMSSD/median | 0.074 (.02) | 0.15 (.03) | 0.08 (.01) |
| Beat-Beat % Change | 4.9 (1.1) | 11.9 (2.3) | 5.5 (1.3) | pNN50 = percentage of R-R intervals which differed by >50 msec;
pBB5% = percentage of successive beats which differed by ≥ 5%;
pBB10% = percentage of successive beats which differed by ≥ 10%;
SD = standard deviation; RMSSD = square root of the mean squared differences of successive intervals;
LF = low frequency;
HF = high frequency

FIG. 14

DETECTION AND CHARACTERIZATION OF CHOLINERGIC OSCILLATORY CONTROL IN PERIPHERAL MICROVASCULATURE

CROSS-REFERENCE TO RELATED APPLICATIONS

This application is a continuation-in-part of International Application No. PCT/US01/43644, filed Nov. 14, 2001, which claims benefit under 35 USC 119(e) to U.S. Provisional Application No. 60/248,009, filed Nov. 14, 2000. These applications here incorporated herein by reference in their entirety.

FIELD OF THE INVENTION

The invention relates to medical devices and techniques in general. More particularly, the invention relates to a method and apparatus for ascertaining the condition of a subject by assessing one or more oscillatory activities of the subject.

BACKGROUND OF THE INVENTION

Overview of Time-Domain and Spectral-Domain Indices

Many biological systems have inherent oscillatory patterns. An example of such an inherent oscillatory pattern is heart rate (HR) variability which is the variation in the time interval between successive beats of the heart. This also may be referred to as respiratory arrhythmia because the periodic slowing and acceleration of HR is synchronous with respiration. A similar oscillatory pattern is seen in blood pressure (BP). Analysis of the oscillatory pattern in the time-domain results in characterizing the oscillatory signal in general statistical terms; for example, HR may be characterized as mean +/− standard deviation (SD). Of note, oftentimes instead of HR (beats/min), the interval between heart beats (R-R interval, in milliseconds) is reported and HR variability (HRV) is expressed as the variability between successive R-R intervals (i.e., as 'R-R variability'). Various prior art methods for assessing HRV are shown in FIG. 3. Unless otherwise stated, the variability in the ECG is expressed as R-R variability in the present disclosure (FIG. 1A).

In addition to the time-domain analysis, an oscillatory signal can be analyzed in the frequency-domain making use of a technique such as Fourier transformation or it can be analyzed according to chaos theory. The oscillatory signal is described as a sum of a series of sinusoidal and cosinusoidal functions of various amplitudes and frequencies to determine an instantaneous-amplitude spectrum. The spectrum, termed the autopower spectral density (APSD), describes the oscillatory signal in terms of the oscillatory power present in each frequency interval and the area under the APSD curve corresponds to the amount or amplitude of each specific fluctuation frequency in the original oscillatory signal. The APSD is calculated by determining the normalized power of a signal from the instantaneous amplitude-spectrum in accordance with the equation (1) below:

$$Gaa = ave(SaSa^*)/df \quad (1)$$

where $Gaa$=instantaneous amplitude spectral density of a sampling channel ("a"); $Sa$=instantaneous amplitude spectrum of channel a; $Sa^*$=complex conjugate of $Sa$; $df$=frequency resolution. For a more detailed discussion of the use of Fourier transformation to describe oscillatory biological signals, the reader may consult Stout, et al., *Anaesthetic Pharmacology and Physiology Review* volume 4, issue 1 pages 96-110, 1996 and U.S. Pat. No. 4,862,361 issued to Gordon, et al. A typical APSD is shown in FIG. 1B.

To perform these analyses for the ECG, one must first determine the precise time of each beat (i.e., of each R-wave). Each R-wave of the ECG is typically identified by the combination of derivative plus threshold detection of the fiducial point of data sampled at 250 Hz (250 times/sec). The successive HR values or R-R intervals are used to generate the 'HR tachogram' or 'R-R tachogram,' respectively, with time on the x-axis and HR or R-R interval on the y-axis. Since the HR and R-R tachograms are not really continuous waveforms (they are generated by sampling the HR or R-R for each beat at 5 Hz), the tachogram is more aptly described as pseudocontinuous. It has discrete, variable-interval data that are converted to a waveform. Thus, the prior art also describes spectral-domain analysis of the ECG in terms of variable-interval, beat-to-beat data, wherein a single data point is plotted at the time of each beat (as opposed to at 5 Hz). This procedure has not been considered to be necessary for treatment of continuous waveforms such as continuous flow and continuous BP. Thus discrete, variable-interval data of these indices has not been utilized for spectral-domain analysis. This invention will include an explanation of the need for performing these steps and a methodology for utilizing discrete, variable-interval data to perform spectral analysis of continuous waveforms.

Autonomic Nervous System

The autonomic nervous system controls many key processes including the activity of cardiac muscle, smooth muscles and glands. It is divided into the parasympathetic nervous system and the sympathetic nervous system. The sympathetic, or adrenergic, nervous system innervates the major organs such as the heart (where it causes increased contractility and increased HR) and blood vessels (where it typically causes vasoconstriction by causing contraction of vascular smooth muscle cells). The parasympathetic, or cholinergic, nervous system also innervates the major organs, such as the heart, where it causes decreased contractility and decreased HR. Prior to the present invention, the parasympathetic nervous system was believed to have minimal effect on the peripheral vasculature.

Oscillatory activities controlled by the branches of the autonomic nervous system will have an inherent frequency that is dependent upon which branch of the autonomic nervous system controls the activity. Oscillatory activity controlled by the sympathetic nervous system is characterized by low frequency (LF) oscillations of less than about 0.12 Hz. The present invention additionally recognizes that oscillatory activity controlled by the parasympathetic nervous system is characterized not only by this low frequency, but also by high frequency (HF) activity as fast as 0.5 Hz. Based on this, the present invention, as described below, is able to determine the presence or absence of sympathetic or parasympathetic activity in an oscillatory signal by analyzing the APSD of the oscillatory signal and determining its power in certain frequency ranges. (see, e.g., FIG. 6 discussed below).

HR variability has both a parasympathetic component and a sympathetic component and thus has characteristic frequency components (FIG. 1B). Analysis of the presence, absence, or quantity of each of these components, i. e., of power in a particular region of the APSD, has been correlated to prognosis in a variety of pathological conditions. A reduction in parasympathetic activity (reduction in high-frequency signal) has been correlated to arrhythmias and a poor prognosis in congestive heart failure (Frey, et al., *J Am*

Coll Cardiol 212:286A, 1993). A similar reduction in parasympathetic activity as evidenced by a reduction in power in the HF region of the $APSD_{R-R}$ has been correlated to a poor prognosis in autonomic neuropathy associated with diabetes (Bernardi, et al., Acta Diabetol Lat. 23:141-54, 1986). In hypertensive subjects, a relatively decreased level of parasympathetic activity in HR variability as may be seen at rest or in response to a sympathomimetic challenge is seen (Furlan, et al., J Hypertens 5:S423-5, 1987). Moreover, declines in the effects of parasympathetic activity on the ECG may precede clinical evidence of hypertension (Markovitz J H, Matthews K A, Kannel W B, Cobb J L: Psychological predictors of hypertension in the Framingham study: is there tension in hypertension? JAMA 1993; 270 (20): 2439-2494; Langewitz W, Ruddel H, Schachinger H: Reduced parasympathetic cardiac control in patients with hypertension at rest and under mental stress. Am Heart J 1994;127:1228-8) and diabetic autonomic neuropathy (Van Ravenswaaij-Arts CMA, Kollée L A A, Hopman J C W, Stoelinga G B A, van Geijn P: Heart rate variability. Ann Intern Med 1993; 118:436-47; Hosking D J, Bennett T, Hampton J R: Diabetic autonomic neuropathy. Diabetes 1978;27: 1043-55; Ewing D J, Campbell I W, Clarke B F: Assessment of cardiovascular effects in diabetic autonomic neuropathy and prognostic implications. Ann Intern Med 1980; 92(part 2):308-11; Bellavere F, Bosello G, Cardone C, Girardello L, Ferri M, Fedele D: Evidence of early impairment of parasympathetic reflexes in insulin dependent diabetics without autonomic symptoms. Diabete Metab 1985; 11:152-6; Pfeifer M A, Cook D, Brodsky J, Tice D, Reenan A, Swedine S, et al.: Quantitative evaluation of cardiac parasympathetic activity in normal and diabetic man. Diabetes 1982;31:339-45; Eckberg D L, Harkins S W, Fritsch J M, Musgrave G E, Gardner D F: Baroreflex control of plasma norepinephrine and heart period in healthy subjects and diabetic patients. J Clin Invest 1986;78:366-374; Duchen L W, Anjorin A, Watkins P J, Mackay J D: Pathology of autonomic neuropathy in diabetes mellitus. Ann Intern Med 1980;92:301-3; Kitney R I, Byrne S, Edmonds M E, Watkins P J, Roberts V C: Heart rate variability in the assessment of autonomic diabetic neuropathy. Automedica 1982;4:155-67; Freeman R, Saul J P, Roberts M S, Berger R D, Broadbridge C, Cohen R J: Spectral analysis of heart rate in diabetic neuropathy. Arch Neurol 1991;48:185-190; Pagani M, Malfatto G, Pierini S, Casati R, Masu A M, Poli M, Guzzetti S, Lombardi F, Cerutti S, Malliani A: Spectral analysis of heart rate variability in the assessment of autonomic diabetic neuropathy. J Auton Nerv Syst 1988;23:143-153; Malliani A, Pagani M, Lombardi F, Cerutti S: Cardiovascular neural regulation explored in the frequency domain. Circ 84:482-489, 1991) as well as associated organ injury. Loss of HF oscillatory activity was associated with poor wound healing in diabetic patients (van den Akker T J, Koeleman A S, Hogenhuis L A, Rompelman O: Heart rate variability and blood pressure oscillations in diabetics with autonomic neuropathy. Automedica 1983;4:201-8) and was the major resistive factor in hypertensive rats (Borders J L: Vasomotion patterns in skeletal muscle in normal and hypertensive rats. Abstract of Dissertation, 1980, Univ. of CA, Berger R D, Saul J P, Cohen R J: Transfer function analysis of autonomic regulation. I. Canine atrial rate response. Am J Physiol 256:H142-H152, 1989). Both conditions are associated with decreased parasympathetic activity (Ewing 1985, Kitney 1982, Paganai JANS 1988; Langewitz 1994; Guzzetti S, Piccaluga E, Casati R, Cerutti S, Lombardi F, Pagani M, Malliani A: Sympathetic predominance in essential hypertension: a study employing spectral analysis of heart rate variability. J Hypertension 1988; 6:711-7), but this was not addressed by those investigators.

Assessment of Oscillations

There are multiple ways to assess oscillations in the peripheral vasculature, including laser Doppler flowmetry (LDF). LDF is a technique for assessing arteriolar and capillary blood flow at the level of the microvasculature. In LDF, laser light at a wavelength absorbed and reflected by hemoglobin is directed onto a tissue such as the skin of the subject and penetrates the surface of the tissue. The light contacts red blood cells and is reflected by moving blood cells; this causes the laser light to undergo a Doppler shift. The flux of the red blood cells through the blood vessels (concentration times velocity) can be calculated by measuring the wavelength shift of the reflected light. Continuous monitoring of the LDF signal delineates the pulsatile changes throughout the course of each heart beat and the superimposed oscillations induced by autonomic activity.

Prior to the present invention, the parasympathetic nervous system was believed to have only a minor role in peripheral vasoregulation and "virtually no effect on peripheral resistance" (Guyton A C, Hall J E: Nervous regulation of the circulation, and rapid control of arterial pressure. In: Guyton A C, Hall J E: Textbook of Medical Physiology, Ninth Edition. WB Saunders Co. Philadelphia, 1996, pp. 209-220; ch. 18). Hence, no one sought to measure oscillations in the peripheral microvasculature as a means of monitoring microvascular cholinergic activity. Instead, HF oscillations in the microvasculature simply were attributed to transmission of atropine-sensitive HF oscillations at the heart (e.g., respiration-induced, cholinergically mediated variations in HR and BP (Pomeranz B, Macaulay R J B, Caudill M A, Kutz I, Adam D, Gordon D, Kilbom K M, Barger A C, Shannon D C, Cohen R J, Benson H: Assessment of autonomic function in humans by heart rate spectral analysis. Am J Physiol 248:H151-H153, 1985; Pagani M, Lombardi F, Guzzetti S, Rimoldi O, Furlan R, Pizzinelli P, Sandrone G, Malfatto G, Dell'Orto S, Piccaluga E, Turiel M, Baselli G, Cerutti S, Malliani A: Power spectral analysis of heart rate and arterial pressure variabilities as a marker of sympatho-vagal interaction in man and conscious dog. Circ Res 59:178-193, 1986; Lossius K, Eriksen M: Spontaneous flow waves detected by laser Doppler in human skin. Microvasc Research 50:94-104, 1995; Akselrod S, Gordon D, Madwed J B, Snidman N C, Shannon D C, Cohen R J: Hemodynamic regulation: investigation by spectral analysis. Am J Physiol 1985; 249:H867-H875; Bernardi L, Hayoz D, Wenzel R, Passino C, Calciati A, Weber R, Noll G: Synchronous and baroreceptor-sensitive oscillations in skin microcirculation: evidence for central autonomic control. Am J Physiol 273:H 1867-H1878, 1997) herein termed $COC_{HR}$) to relatively passive vascular beds. (Hertzman A B, Roth L W: The absence of vasoconstrictor reflexes in the forehead circulation. Effects of cold. Am J Physiol 136:692-697, 1942; Lossius K, 1995; Bernardi L, 1997).

SUMMARY OF THE INVENTION

Using LDF to delineate microcirculatory changes, the present inventors have confirmed that systemic infusion of the alpha-adrenergic agonist phenylephrine elicits disparate microvascular responses, with intense vasoconstriction of the adrenergically rich finger and maintenance of baseline perfusion in regions without such adrenergic predominance such as the forehead. Maintenance of forehead perfusion was previously associated with emergence of HF oscillations similar to HF forehead oscillations during hyperventilation (Smits T M, Aarnoudse J G, Geerdink J J, Zijlstra W G: Hyperventilation-induced changes in periodic oscillations in forehead skin blood flow measured by laser Doppler flowmetry. Int J Microcirc: Clin Exp 6:149-159, 1987), arousal (Nordin M: Sympathetic discharges in the human supraorbital nerve and their relation to sudo- and vasomotor responses. J Physiol 423:241-255, 1990), and remote cooling (Nordin M, 1990) and to HF regional oscillations during post-occlusion hyperemia (Wilkin J K: Poiseuille, periodicity, and perfusion: rhythmic oscillatory vasomotion in the skin. J Invest Dermatol 93:113S-118S, 1989; Meyer J-U, Borgstrom P, Lindbom L, Intaglietta M: Vasomotion patterns in skeletal muscle arterioles during changes in arterial pressure. Microvasc Res 1988;35: 193-203) and cerebral vasoconstriction (Hudetz A G, Roman R J, Harder D R: Spontaneous flow oscillations in the cerebral cortex during acute changes in mean arterial pressure. J Cerebral Blood Flow Metab 1992;12:491-499). The unique finding of the present invention was that HF forehead oscillations induced by phenylephrine were eliminated by the anti-cholinergic drug atropine, thereby indicating cholinergic transmission with the neurotransmitter acetylcholine. The effect of atropine was not tested in the prior art, presumably because— despite its vital contribution to sympathovagal balance at the heart and its involvement in thermal reflexes (Roddie I C: Circulation to skin and adipose tissue, Handbook of Physiology; Section 2: The Cardiovascular System—Peripheral Circulation and Organ Blood Flow, Vol. 3. Edited by Shepherd J T, Abboud F M, Geiger S R. The American Physiology Society, Bethesda, Md., pp 285-316, 1983; Roddie I C, Shepherd J T, Whelan R F: The contribution of constrictor and dilator nerves to the skin vasodilatation during body heating. J Physiol 136:489-497, 1957), isolated local reflexes (Ito B R, Feigl E O: Carotid baroreceptor reflex coronary vasodilation in the dog. Circ Res 56:486-495, 1985; Zucker I H, Cornish K G, Hackley J, Bliss K: Effects of left ventricular receptor stimulation on coronary blood flow in conscious dogs. Circ Res 1987;61:11-54-II-60) and "local functional hyperemia" (Bell C: Cholinergic vasodilator mechanisms. pp. 59-74, chapter 2. In: Nervous Control of Blood Vessels, edited by Bennett T, Gardiner S M. Australia: Harwood Academic Publishers, 1996)—acetylcholine has been considered an "outcast as a vasomotor transmitter" (Bell, 1996).

If challenge-induced HF microcirculatory oscillations were the consequence of extension of the association between HR and BP to the microvasculature, then oscillations of HR and those detected by LDF should exhibit coordinated changes in amplitude and/or frequency. However, as detailed below, the present inventors have documented a lack of association between $COC_{HR}$ and HF oscillations in the microvasculature of certain regions such as the forehead and forearm (herein termed $COC_{micvasc}$). This indicates that HF microvascular oscillations are not due to transmission from the heart and confirms that $COC_{micvasc}$ actually represents a previously unrecognized, locally mediated cholinergic microvascular process. The present inventors have documented a peripheral neurovascular etiology to this process by demonstrating loss of the oscillatory activity upon topical application of local anesthetic. This is supported by documentation of the oscillatory activity in the absence of heart or lung function during cardiopulmonary bypass. The present invention not only describes the inventive means to identify and characterize this process but also inventive means to compare and contrast it to other oscillatory processes such as $COC_{HR}$.

The present invention changes the classic separation of the APSD of HR, BP, and flow waveforms from the traditional LF (0-0.12 Hz) and HF (0.12-0.50 Hz) categories to LF (0-0.12 Hz), IF (intermediate frequency, approximately 0.12-0.18) and RF (respiratory frequency, 0.18-0.50 Hz) categories that facilitate characterization of parasympathetic activity in the peripheral vasculature which is centered primarily in the IF range.

The present invention provides the means to identify and characterize $COC_{micvasc}$ and to compare and contrast the time-domain and spectral-domain features of a process such as $COC_{micvasc}$ to comparable features of another process (such as $COC_{HR}$). In one embodiment, the invention includes a method of assessing a condition of subject's parasympathetic nervous system. In the inventive method, the subject is exposed to a physiologic challenge, and the oscillatory activity of a plurality of blood vessels disposed in a peripheral region of a subject's vascular system is measured. The measuring step is performed by probing the plurality of blood vessels with an interrogation signal (e.g., using LDF), receiving a reflected signal from the plurality of blood vessels, and evaluating characteristics of the reflected signal in the IF band. A condition of the parasympathetic nervous system of the subject is then determined from this measurement. As discussed below, this assessment may then be used, inter alia, to diagnose diabetic autonomic neuropathy or as a pre-hypertensive screening tool.

The present invention provides means to monitor oscillatory activity of the microvasculature in a region of cholinergic innervation and characterize oscillatory activity with respect to overall variability, frequency(s) of oscillatory activity, and amplitude and frequency-specific power of oscillatory activity.

Features essential to many of the means of assessment/comparison and clinical application of the newly discovered (herein described) cholinergic oscillatory control of the microvasculature include: 1) improved spectral resolution by delineation of the frequency bin associated with the greatest oscillatory power ("maxbin") within the intermediate frequency band; 2) conversion of continuous, pseudo-continuous and discrete variable-interval data to a common format for interphase, intersite, interpatient, and intermonitor comarison; 3) normalization to common units to optimize such comparisons; and 4) use of techniques such as graphic time-domain and joint time-frequency analysis to enable rapid temporal delineation of oscillatory responses.

In one embodiment, the traditional HF frequency band of the APSD is subdivided into intermediate frequency (IF; approximately 0.12-0.18 Hz) and respiratory frequency (RF; 0.18-0.30 Hz) bands so as to be able to isolate the most relevant band. The bin within a given band that has the maximum oscillatory power (termed 'maxbin') is identified so as to isolate the most relevant bin and thereby avoid 'dilution' of maxbin power by the lesser power of other frequencies.

In accordance with one aspect, the present invention converts the pseudocontinuous R-R tachogram and continuous flow or pressure waveform (e.g. as generated by laser Doppler flowmetry or continuous pressure waveform manometry) to equivalent signals for time-domain and spectral-domain analysis. In addition to treating both the R-R and flux signals as continuous signals (i.e., by resampling R-waves of ECG and continuous flow signal of laser Doppler at 5 Hz as per prior art), the invention uses an algorithm for conversion of continuous signals to discrete variable time-interval signals which are expressed on a beat-to-beat basis (and thus suitable for comparison with variable time-interval data generated from psuedocontinuous data such as the HR or R-R tachogram).

In accordance with a further aspect, the present invention normalizes time-domain and spectral-domain indices so as to facilitate comparisons between baseline and challenge states, healthy vs. diseased tissues, healthy vs. compromised individuals (e.g., patients with hypertension, autonomic neuropathy of diabetes, atherosclerotic injury of vessels), baseline and medicated conditions, between different monitoring sites, and among different monitoring parameters (e.g., $COC_{micvasc}$ vs $COC_{HR}$).

In a particularly preferred embodiment, the present invention normalizes signals prior to generation of APSD or time-domain indices or other means of analysis such as joint time-frequency analysis, and then determines one or more of the following based on the normalized data: APSD; other spectral domain indices such as the cross power spectral density (CPSD); measures of randomness, chaos and control; and time-domain assessments of variability such as the standard deviation (SD), root mean square of successive differences (rmssd), and pNN50 (% of successive beats with at least a 50 msec difference in the successive R-R intervals.) In accordance with still further aspects, normalization and comparison of power in the APSD after generation of the APSD (e.g., express oscillatory power in each bin as a % of mean power/bin for all bins at baseline) is performed. Similarly, normalization and comparison of time-domain indices after determination of standard (prior art) indices (e.g., dividing the SD, rmssd, or related index by the mean or median value of the given parameter during the given assessment phase) may also be used.

In accordance with a further aspect, the invention provides a method for adjusting an overall time-domain variability determination for the oscillatory power at a desired frequency or within a desired frequency range so as to assess relative variability that is attributable to the given oscillatory process during a given phase, at a given monitoring site, and for a given monitoring technique as well as for comparison among phases, sites, and techniques. Representative cutoffs for assessment of the aforementioned differences and changes are also provided.

Whereas time-domain and spectral-domain analysis of cardiovascular waveforms traditionally have been evaluated over an extended period of time, in many settings it would be of critical value to be able to assess the presence of parasympathetic activity in a very brief interval (in that the response may be transient and/or offsetting responses would tend to offset different signals and make them difficult to discern). In accordance with a further aspect, the invention provide a means for delineating normalized changes in a real-time graphic display of beat-to-beat percent changes. In a further aspect, which is designed to further improve the delineation of spectral-domain changes at the desired frequency, the inventions provides means for utilizing joint time-frequency analysis to enable documentation of dynamic changes in the harmonic content of cardiovascular waveforms.

With these and other advantages and features of the invention that will become herein after apparent, the nature of the invention may be more clearly understood by reference to the following detailed description of the invention, the appended claims and to the several drawings attached herein.

BRIEF DESCRIPTION OF THE DRAWINGS

FIG. 1A shows a typical R-R tachogram. FIG. 1B shows the oscillatory influences of parasympathetic and sympathetic pathways on the sinus node of the heart and, as a consequence, HR variability. The upward arrow points toward prior art time-domain indices of HR variability. The downward arrow points to the effect of the prior art steps of converting an electrocardiogram (ECG) to a tachogram and then converting the oscillatory pattern of the tachogram to display the autopower spectral density (APSD). Frequency of oscillations are on the x-axis and oscillatory power at each frequency is on the y-axis. Note, the typical LF and HF peaks in the APSD.

FIG. 5A is a graph of the R-R during BASE and PHENYL, with time (a 50-sec portion of each 200-sec phase) on the x-axis and R-R intervals (ranging from 700 to 1100 msec) on the y-axis. FIG. 5B is a frequency-domain representation of the signals shown in FIG. 5A; the $APSD_{R-R}$ includes the entire 200-sec BASE and PHENYL segments with oscillatory frequency on the x-axis and power (msec$^2$/Hz) on the y-axis. FIG. 5C is a graph of the forehead flux during BASE and PHENYL, with time on the x-axis and flux (over a 5-volt range) on the y-axis. FIG. 5D is a frequency domain representation of the signals shown in FIG. 5C. In particular, FIG. 5D shows an $APSD_{FOREHEADFLUX}$ of 200-sec BASE and PHENYL segments, with frequency on the x-axis and power (volt$^2$/Hz) on the y-axis. Note that in FIGS. 5A and 5B, oscillatory activity at the respiratory frequency persists, while in FIGS. 5C and 5D, phenylephrine-induced activity at approximately 0.14 Hz in forehead flux emerges.

FIGS. 8A, 8B depict a diagram showing normalization of APSD data. This figure compares the normalized powers in the $APSD_{R-R}$ and $APSD_{FOREHEADFLUX}$ during infusion of phenylephrine based upon normalization to mean power/bin during BASE (FIG. 8A) and during PHENYL (FIG. 8B), respectively.

FIG. 9A depicts $APSD_{RESPIRATION}$. FIG. 9B depicts $APSD_{R-R}$. FIG. 9C depicts $APSD_{RADIAL\ ARTERY\ BP}$. FIG. 9D depicts $APSD_{FINGER\ BP}$ (obtained with a FINAPRES, Ohmeda Monitoring Systems, Boulder Colo.). FIG. 9E depicts $APSD_{FINGER\ PLETHYSMOGRAPH}$ (obtained with a standard pulse oximeter). FIG. 9F depicts $APSD_{FINGER\ FLUX}$. FIG. 9G depicts $APSD_{FOREHEAD\ FLUX}$ with its peak at 0.14 Hz, which is different from the center frequency of HF power in the other monitors. FIG. 9H depicts $APSD_{FOREARM\ FLUX}$, which has mixed power, including power within the IF band (similar to the forehead).

FIG. 10A illustrates the raw signal from two different forehead sites which oscillated out of phase from one another. FIG. 10B illustrates the corresponding $APSD_{FOREHEADFLUX}$ for these sites.

FIG. 11A shows normalized data at base levels. FIG. 11C shows normalized data after administration of phenylephrine. FIGS. 11B and 11D show APSD and CPSD displays of R-R and flux under baseline and phenylephrine conditions, respectively. The CPSD is calculated by determining the normalized power of a signal from the instantaneous amplitude-spectrum using the following equation: Gab=ave(SaSb*)/df where Gab=instantaneous amplitude spectral density of the sampling channels; Sa=instantaneous amplitude spectrum of channel a; Sb*=complex conjugate of Sb; df=frequency resolution.

FIGS. 12A-D contain a composite of time-domain graphs showing oscillations of R-R (top) and forehead flux (bottom) generated by conversion of raw R-R and flux data (left) to beat-to-beat % change (right) for the subject of FIG. 5. This facilitates comparison of different phases and different parameters on the same or similar axes to facilitate the inventive comparisons described herein. The ability to determine the oscillatory frequency from a brief segment of data may obviate the need for a relatively long period of data collection to perform spectral domain analysis. Frequency may be measured and the power estimated by measuring the oscillatory amplitude. The horizontal lines represent potential cutoff points that, in light of the inventive process of graphing different indices on the same axes, can be used to determine the incidence with which a given parameter exceeds a certain cutoff during different phases or the incidence with which different monitoring indices exceed such a cutoff. The incidence can be determined by visual inspection (for peak, zero crossings, etc.) or a computerized algorithm. Note, this is a good way to filter out the effect of mean on ultra-low frequency spectra (since beat-to-beat % change is centered at 0%.) It also serves as a way of filtering since the analysis looks at % change, not absolute values. Moreover, it provides a unique and convenient method to discard data by establishing guidelines for acceptable data (e.g., beat-to-beat % change cannot exceed 100% for a given data point).

Following are the basic steps involved in the procedure:
1. Identify R waves.
2. Establish R waves as the timing channel.
3. Treat other waveforms as discrete variable-interval data and synchronize them according to sequential R-R intervals.
4. Determine indices such as max, min, mean, max-min of the synchronized "waveforms" on a beat-by-beat basis by identifying max and min values for each beat and determining other indices with standard statistical techniques.

5. Calculate normalized index for comparisons:

$$\{[(\max \text{ of beat}_{n+1}) - (\max \text{ of beat}_n)]/\max \text{ of beat}_n\} \times 100$$

FIGS. 13A-D are a comparison of APSD before and after normalization according to the method described and illustrated in FIGS. 12A-D. There figures illustrate the APSD generated for R-R and forehead flux based upon the continuous flux and pseudocontinuous R-R "raw" data resampled at the traditional rate of 5 Hz (left) and the inventive beat-to-beat % change discrete, variable time-interval data (right) which facilitates comparisons of the power of different indices on the same axes. Comparison of R-R and flux with new APSD ($APSD_{b\text{-}to\text{-}b\%changeR\text{-}R}$ and $APSD_{b\text{-}to\text{-}b\%changeflux}$) shows that the relative power of oscillatory behavior was comparable at baseline. This allows better appreciation of phenylephrine-induced changes. The persistent predominance of power at 0.2 Hz in the $APSD_{\%b\text{-}to\text{-}bR\text{-}R}$ as well as the emergence of power during PHENYL at approximately 0.14 Hz in $APSD_{\%b\text{-}to\text{-}bFLux}$ are consistent with that noted by more traditional analyses (e.g., FIG. 5, wherein $APSD_{R\text{-}R}$ was based upon pseudocontinuous data, and $APSD_{FLUX}$ was based on continuous data). In addition, data normalized as per the method described in FIG. 12 could be used for other means of comparative assessment such as joint time-frequency analysis.

FIG. 14 is a table of results which show the effects of normalization of time-domain indices during the baseline and challenge phases in eight volunteers who received an infusion of phenylephrine, in accordance with the present invention.

Figures 15A, 15B:
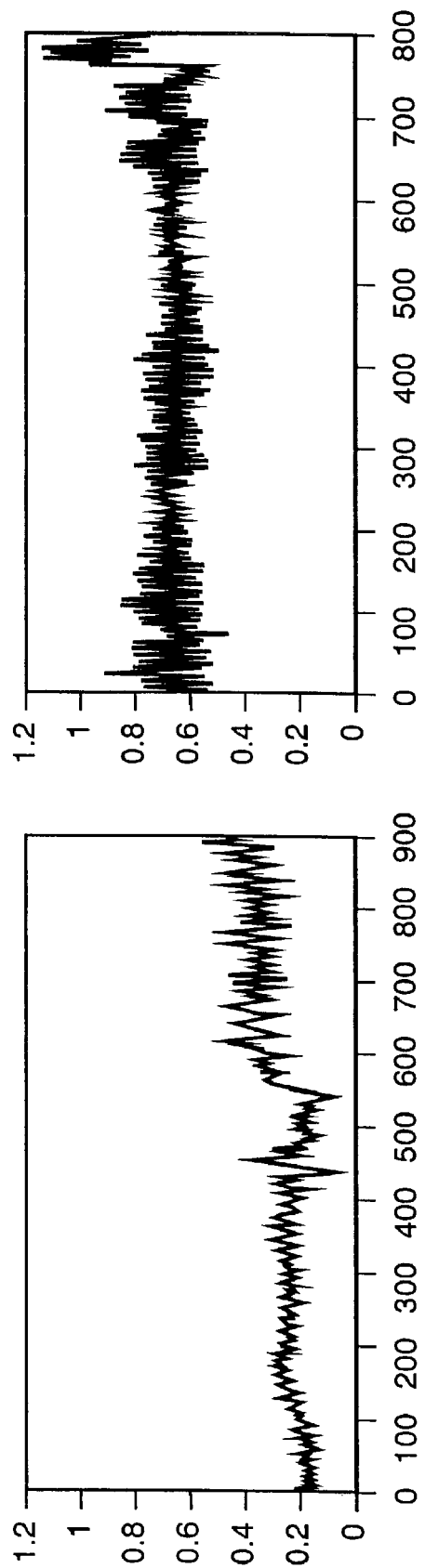
Figure 15D:
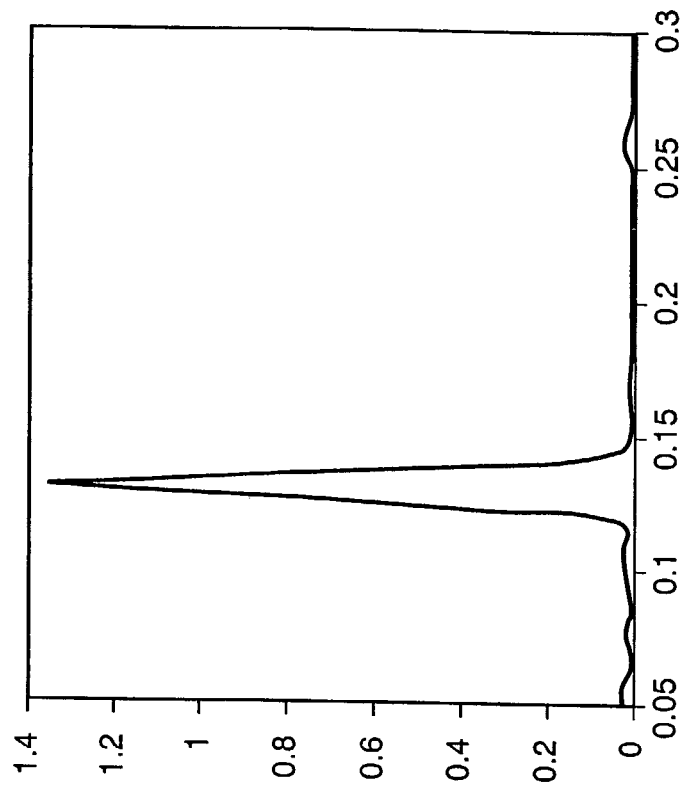
Figure 15C:
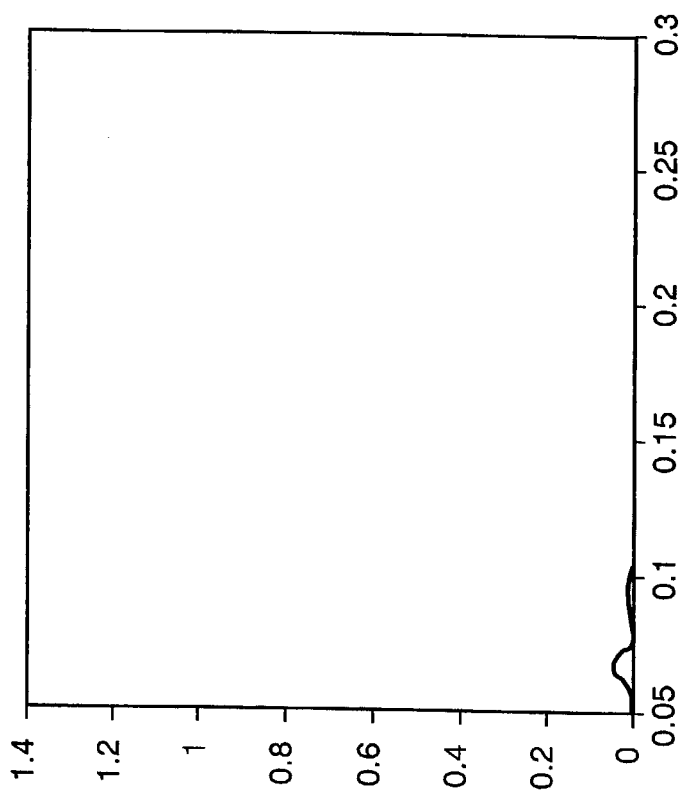

FIGS. 15A-D represent composite data demonstrating how the invention may be used to diagnose diabetes. This is sample data collected during cardiopulmonary bypass, looking at differences between autonomically intact subjects, and individuals with advanced diabetes. Data was collected using a laser Doppler measuring face flux, during bypass, when there is no cardiac or respiratory activity. At the end of the bypass period, patient's body temperature is warmed back up to the normal range (it's cooled early on during bypass). During rewarming, periods of relatively large amplitude oscillation in patients who are autonomically intact tend to be seen. FIG. 15A is laser Doppler face flux during rewarming in a diabetic subject. FIG. 15B shows a non-diabetic during the same period. FIGS. 15C, 15D are the APSDs for each flux pattern. The diabetic patient (FIG. 15C) shows no peak in the parasympathetic range, and almost no power anywhere between 0.05 and 0.3 Hz. The intact patient (FIG. 15D) shows relatively high power, nearly all at the 0.13 Hz peak. This demonstrates an intact parasympathetic homeostatic mechanism in the latter patient, which is notably absent in the former.

Figure 16A:
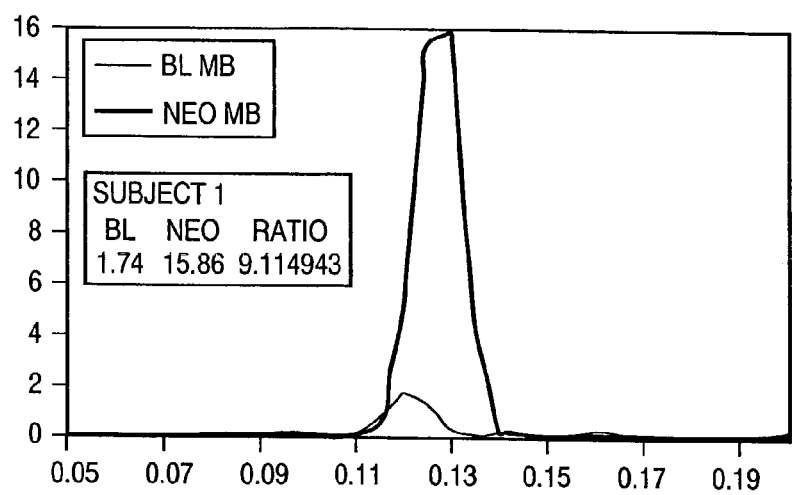
Figure 16B:
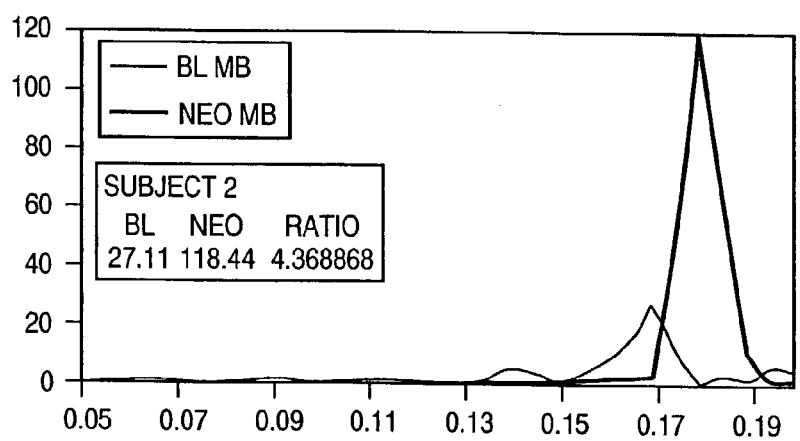
Figure 16C:
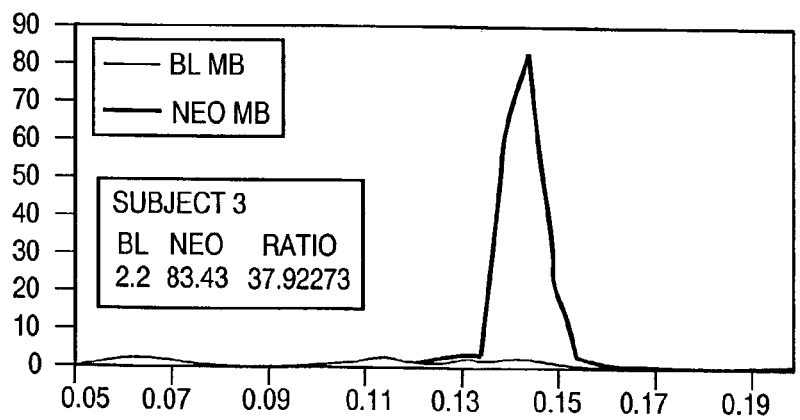

FIGS. 16A-C represent composite data demonstrating how the invention may be used as a prehypertensive screening tool. Laser Doppler flowmetry (flux) of the face in non-hypertensive, autonomically intact subjects, shows little or no oscillatory activity when the patient is in a baseline (non-physiologically challenged) state. This is seen in the autopower spectral density (APSD) analysis as very low amplitude peak (compared with the peak amplitude during a parasympathetic challenge) in the 0.12-0.18 Hz range. Consequently, the ratio of the phenylephrine-induced peak amplitude to the baseline peak amplitude would be relatively high (say, greater than 15, maybe as high as 30 or more). In borderline or undiagnosed early hypertensives, it is believed that the parasympathetic nervous system is activated, coordinating peripheral vasculature, resulting in an autonomic homeostatic attempt to normalize the blood pressure. This is manifested by higher peak APSD power in the 0.12-0.18 Hz range at baseline, and hence a lower phenylephrine/baseline ratio compared to the phenylephrine parasympathetic challenge (ratios less than 10 or so).

Figure 17:
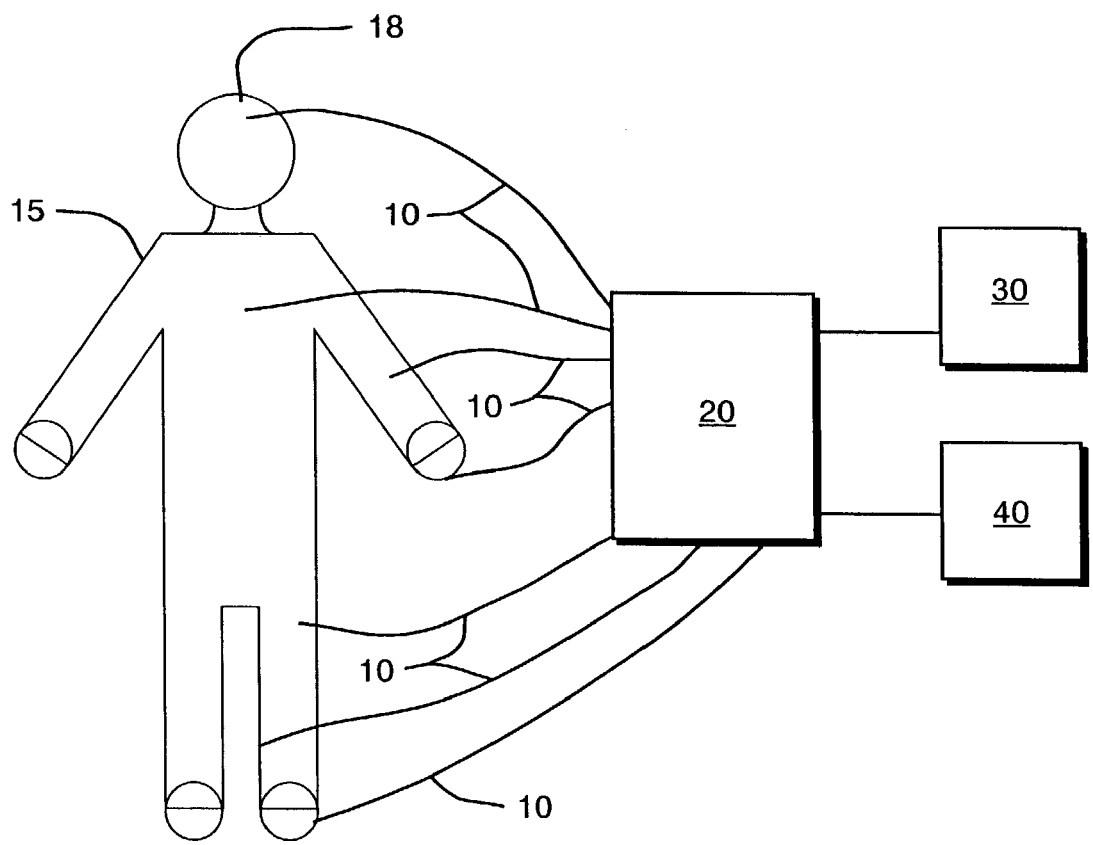

FIG. 17 shows a system for monitoring and characterizing a subject's oscillatory control in peripheral microvasculature, in accordance with the present invention.

Figure 18:
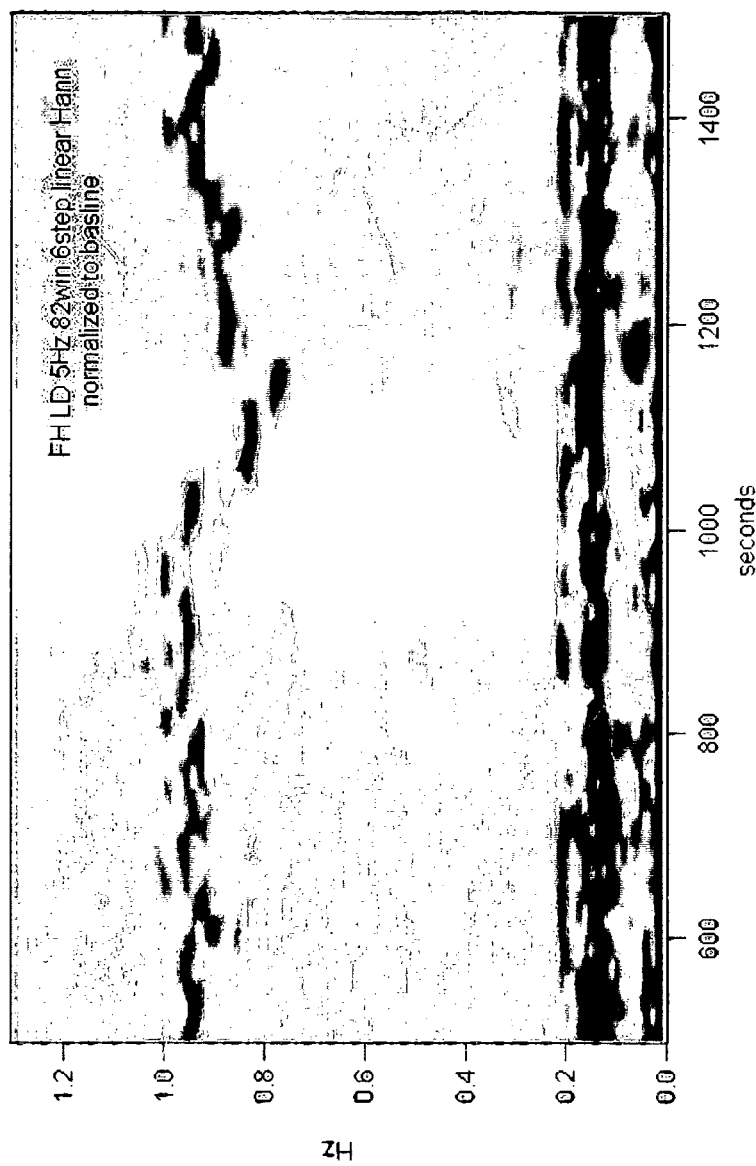

FIG. 18 shows the gray scale joint time-frequency display of oscillatory activity in the forehead with: time (sec) on the x-axis; frequency (based on resolution, in Hz) on the y-axis; and intensity of power expressed as darkness of the given frequency response. Note, first, the dark line at approximately 1 Hz, representing the pulsation with each heart beat; the frequency changes after the injection of phenylephrine, indicative of a decline in heart rate. Note, too, the increase in power in the intermediate frequency range (0.12-0.18 Hz) at approximately the same time as the decline in heart rate.

Figure 19:
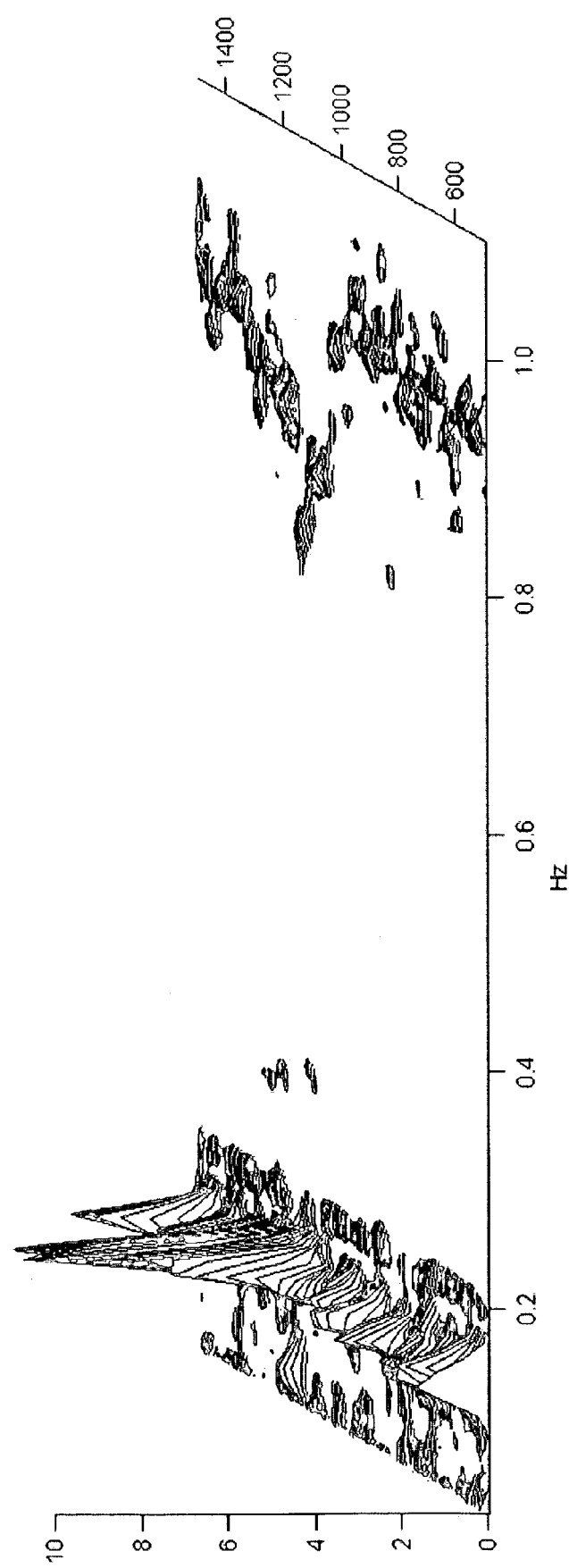

FIG. 19 uses a waterfall display to illustrate the transient change in power after phenylephrine. Frequency is on the x-axis; time is on the y-axis; and power is on the z-axis.

Figure 20:
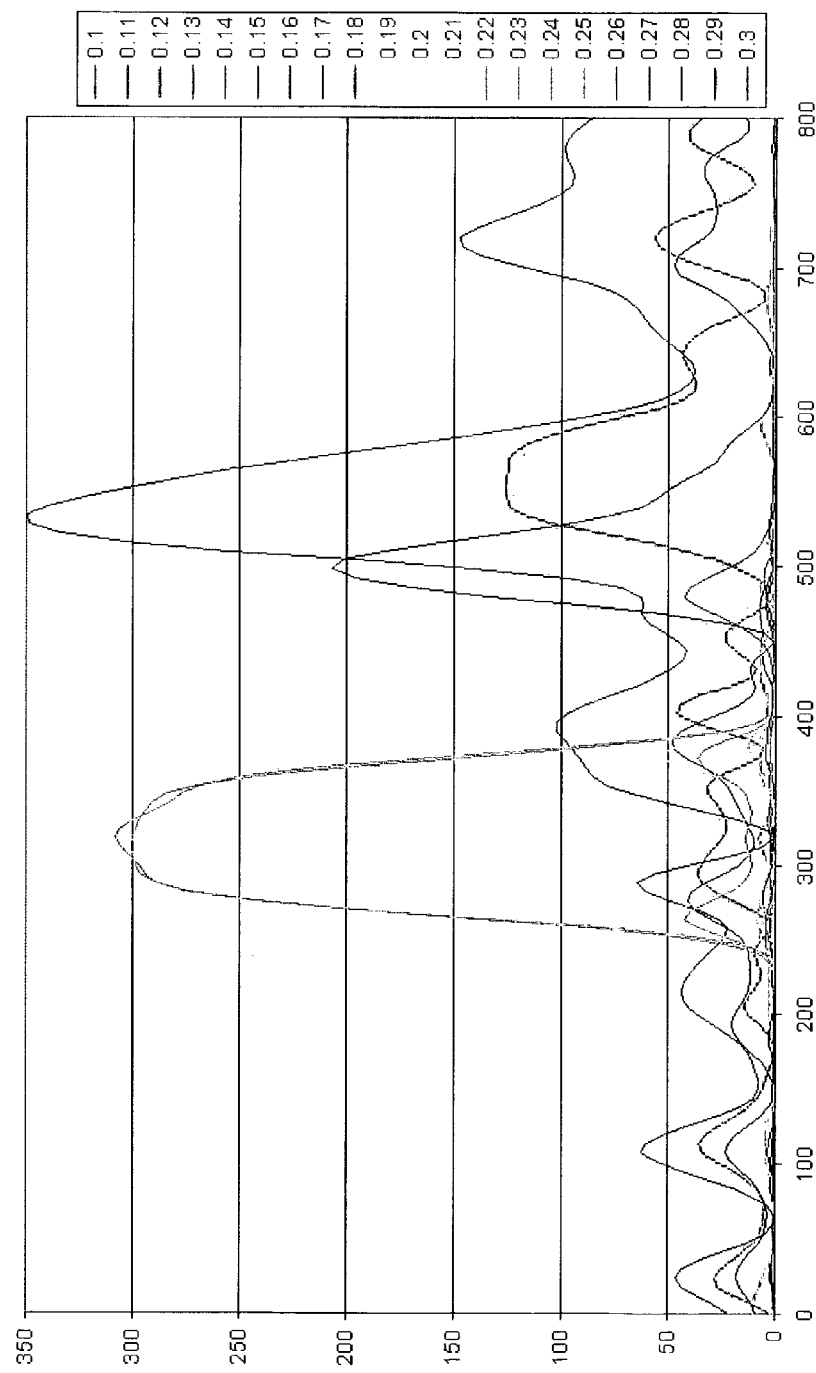

FIG. 20 provides a joint time-frequency analysis of the data collected on a patient (data not provided).

DETAILED DESCRIPTION OF THE PREFERRED EMBODIMENTS

The present invention provides methods and apparatuses to monitor the condition of a subject by determining and analyzing the character of one or more oscillatory signals in one or more portions of the subject. In some embodiments, at least one oscillatory signal will be determined in a peripheral region of the subject. In some preferred embodiments, the peripheral region of the subject may be the forehead microvasculature.

General Analytical Framework

In general, the methods of the present invention involve determining an oscillatory activity in one or more portions of a subject's anatomy and evaluating that activity in order to deduce information concerning the condition of the subject. As discussed above, oscillatory activities have an inherent frequency that is dependent, in part, upon how the activity is controlled by the autonomic nervous system. Thus, analysis of oscillatory activities provides information concerning conditions that have an autonomic component. The presence, absence or amount of an activity of a characteristic frequency has been correlated to various pathological conditions. The leading example of this type of correlation is seen in analysis of heart rate (HR) variability.

The present invention has improved upon the prior art determination of oscillatory activities by facilitating the acquisition of data from the peripheral regions of the subject. Prior to this invention, it was not known that oscillatory data representative of parasympathetic activity could be acquired in the peripheral microvasculature. As seen in the following examples, it is now possible to obtain information concerning the cholinergically mediated pathways (e.g., the parasympathetic nervous system of a subject) by monitoring oscillatory activity in a peripheral region of the subject. Using correlation between the characteristics of the autonomic nervous system and the condition of the subject, it is now possible to diagnose various conditions based upon characteristics of oscillatory activities in the periphery of the subject.

Figure 5A:
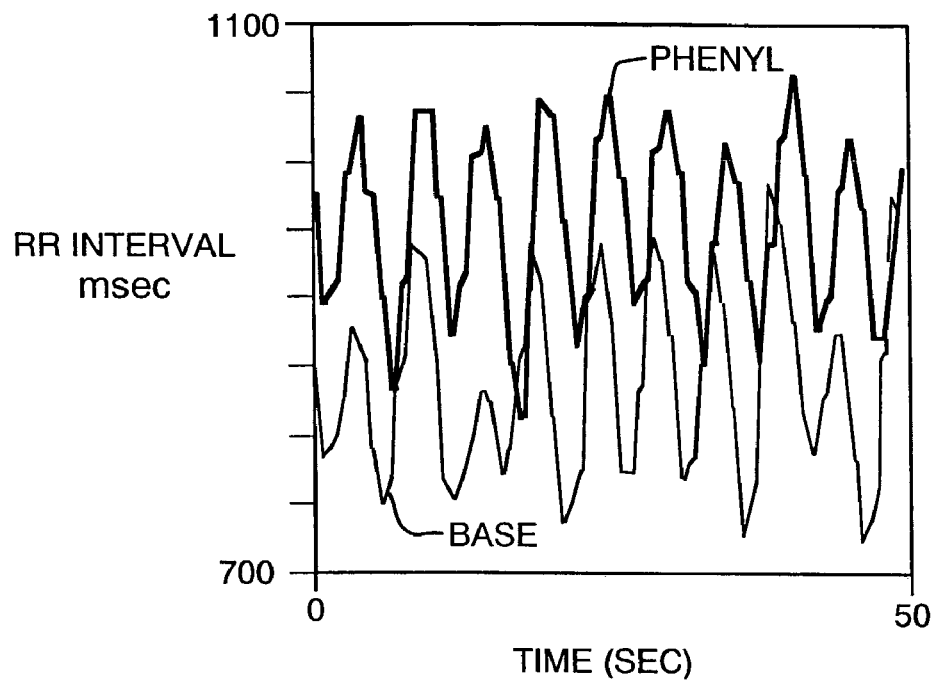
FIGS. 5A-5D depict data indicating that phenylephrine induces activity at approximately 0.14 Hz in the forehead, and include a composite showing the R-R interval and forehead flux in a single subject during metronome breathing (at a rate of 1 breath/5 seconds or 0.20 Hz), at baseline (BASE, light line), and during infusion of phenylephrine (PHENYL, dark line).
Figure 5B:
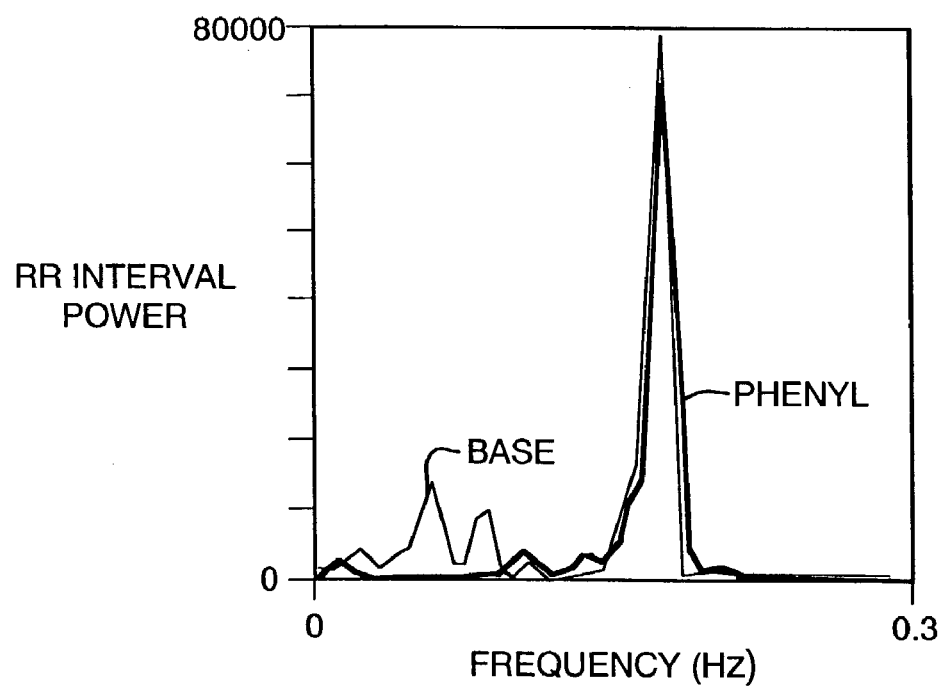
Figure 5C:
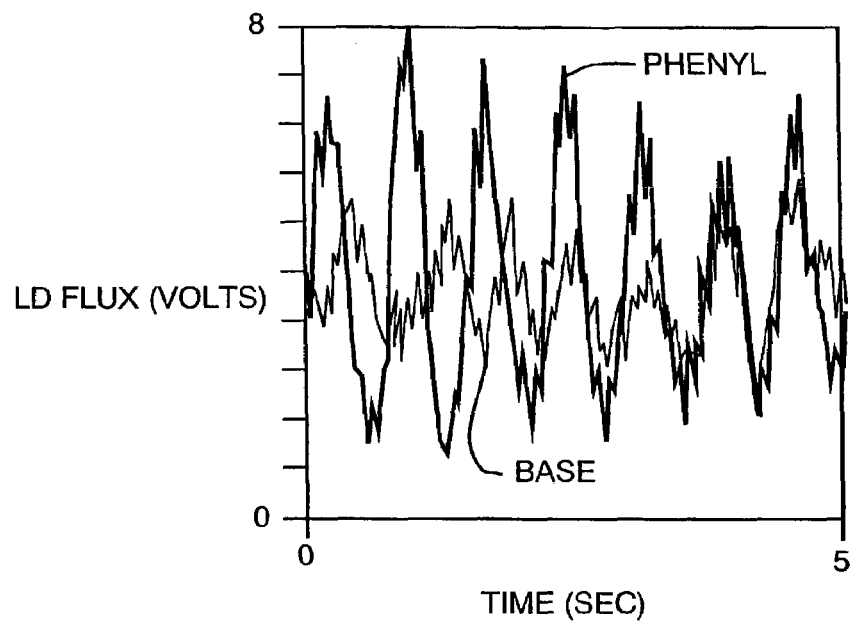
Figure 5D:
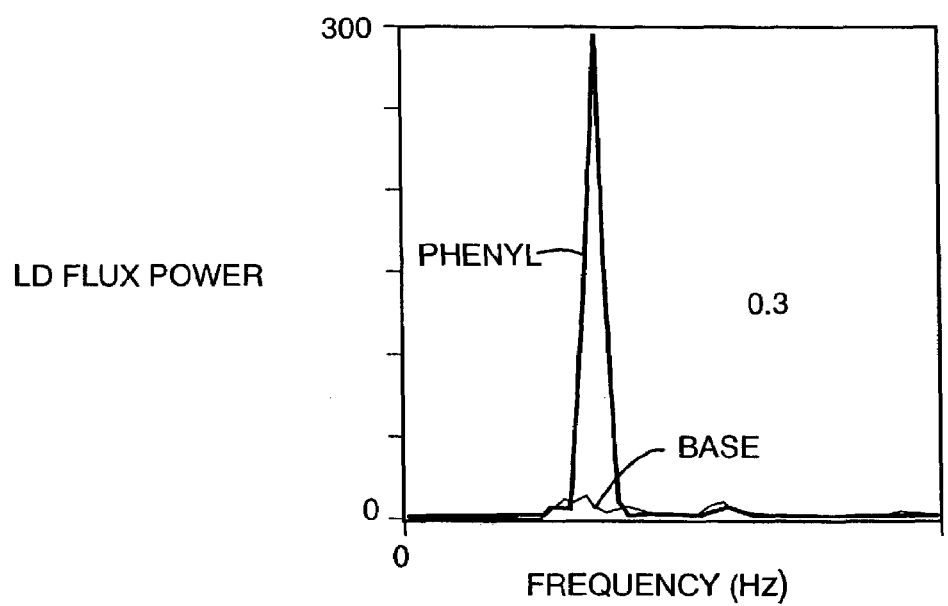
Figure 6:
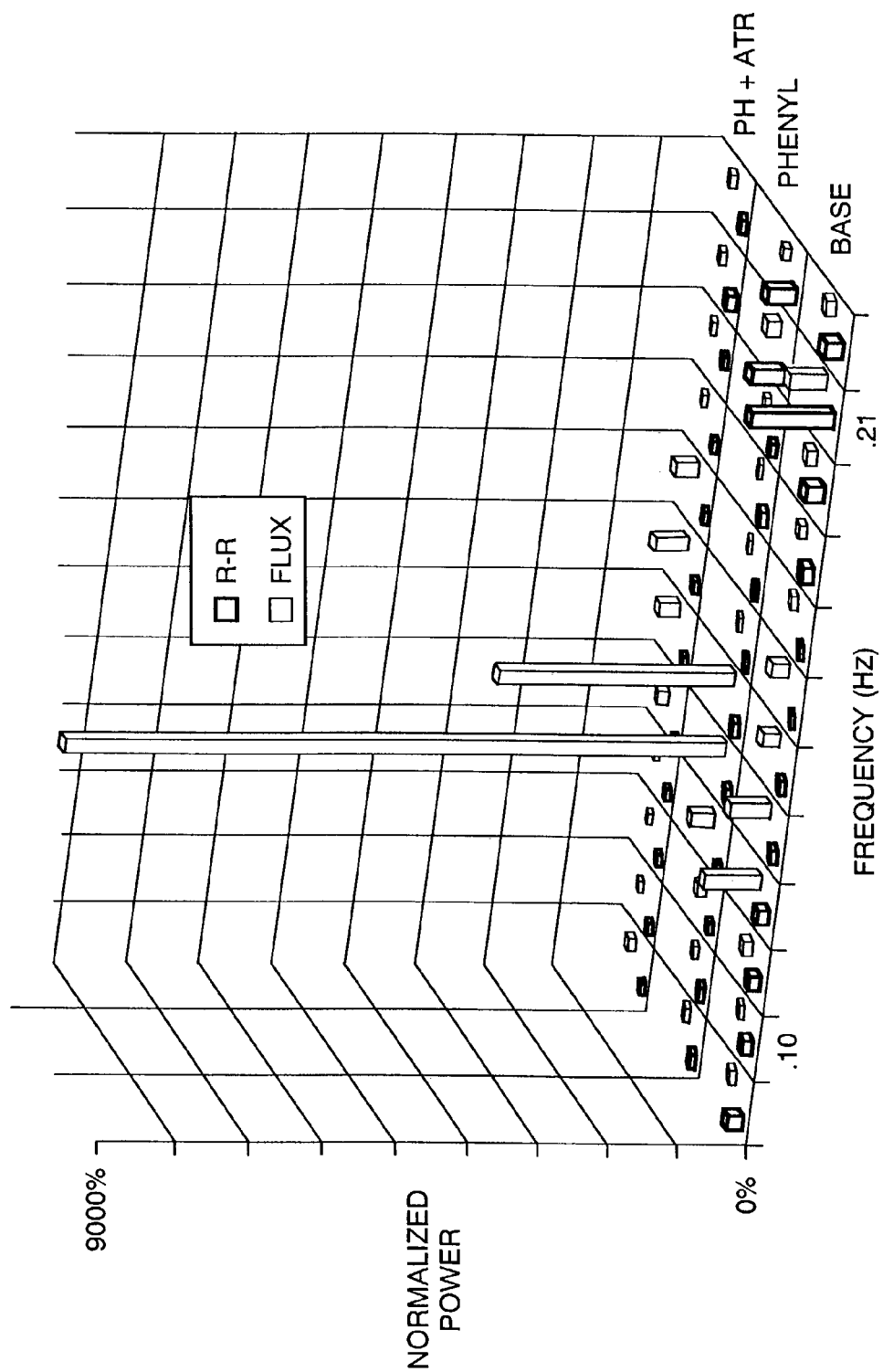
FIG. 6 is a diagram depicting normalized APSD power for the subject in FIG. 5. This is a composite showing normalized power in the 0.01 Hz bins between 0.10 and 0.21 Hz in the $APSD_{R-R}$ (dark bar, left side of each bin) and $APSD_{FOREHEADFLUX}$ (light bar, right side of each bin) during each phase. Data from baseline conditions (BASE) are shown in front, phenylephrine phase (PHENYL) is show in the middle, and phenylephrine plus atropine (PH+ATR) is shown in the rear. Note the similar power in the $APSD_{R-R}$ at approximately 0.20 Hz during BASE and PHENYL as well as the PHENYL-induced emergence of power in the $APSD_{FOREHEADFLUX}$ at approximately 0.14 Hz. Although two adjacent peaks are shown in the $APSD_{FOREHEADFLUX}$ in the 0.14 Hz and 0.15 Hz bins in the PHENYL phase of this subject, a predominant single peak was obtained when the two adjacent 0.005 Hz-wide bins (i.e., 0.145-0.150 Hz and 0.150-0.155 Hz bins) with the greatest power were combined to form what is termed "maxbin" in the present application.
Figure 7:
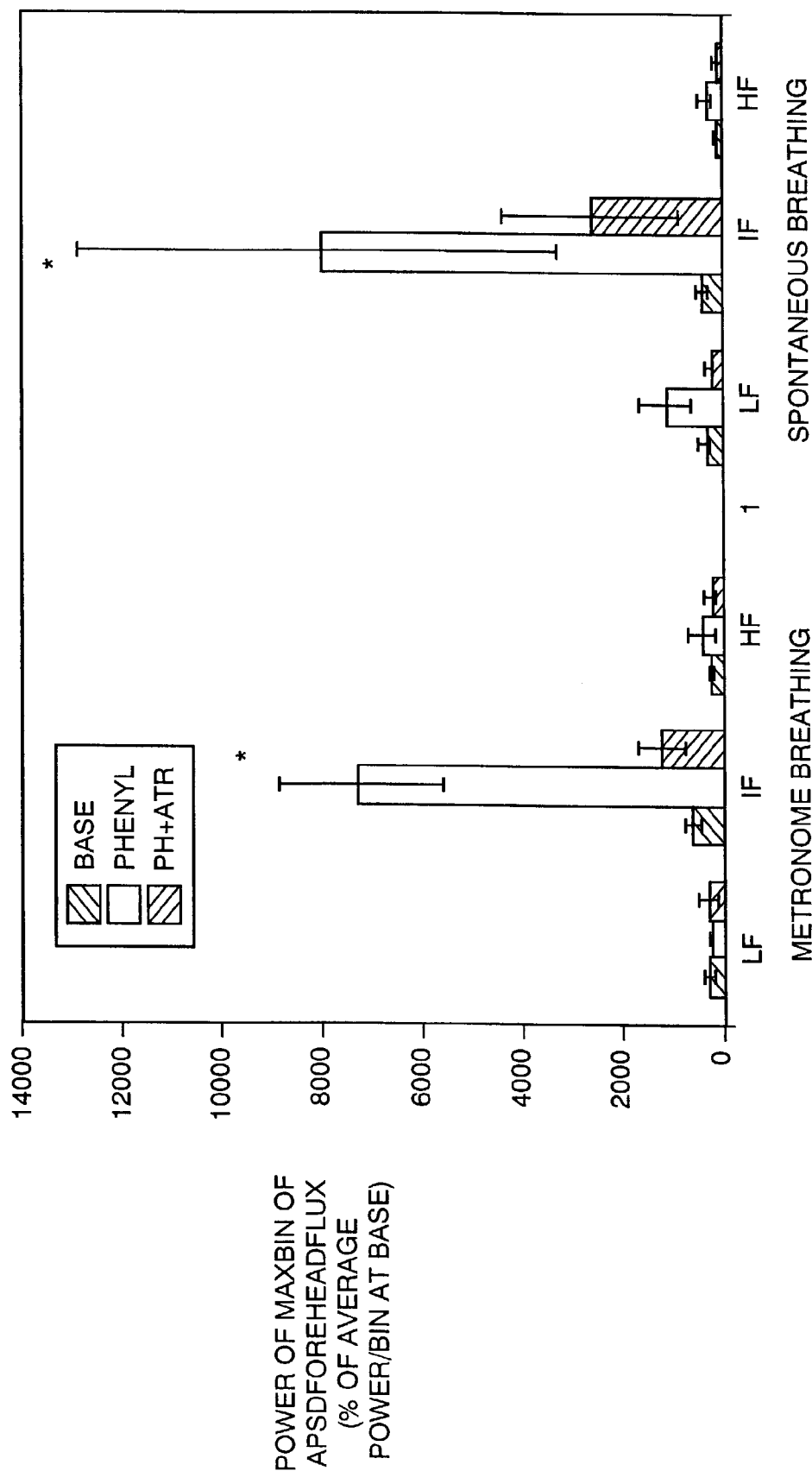
FIG. 7 is a diagram depicting maxbin power of $APSD_{FOREHEADFLUX}$ during the BASE, PHENYL and PH+ATR phases. Power/bin is expressed as a % of the mean power/bin during the corresponding pattern of respiration during BASE. Bins are 0.01 Hz wide. Bars represent mean (standard error) of "maxbin" values in each band during each phase (n=8 subjects).
Figure 9A:
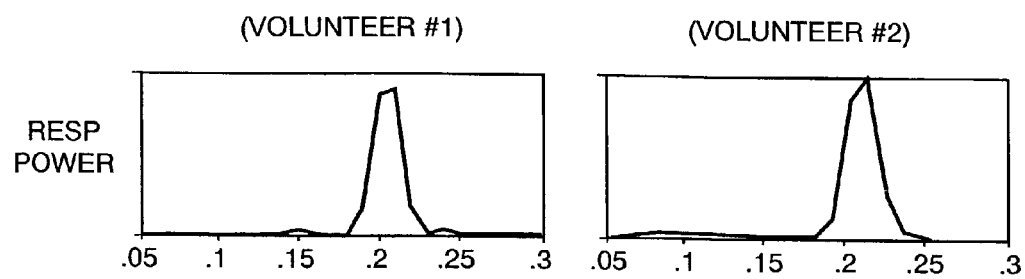
FIGS. 9A-H represent composite data indicating that phenylephrine-induced parasympathetic activity at the forehead is not transferred from more proximal sites in the body. This is a composite of graphs showing the APSD of multiple monitoring parameters after administration of phenylephrine to two volunteers breathing at 0.20 Hz. Frequency (Hz) is on the x-axis and power ($msec^2$/Hz for R-R, $mmHg^2$/sec for BP, and $volts^2$/Hz for all other indices) is on the y-axis. Data from volunteer #1 are shown on the left and data from volunteer #2 are shown on the right.
Figure 9B:
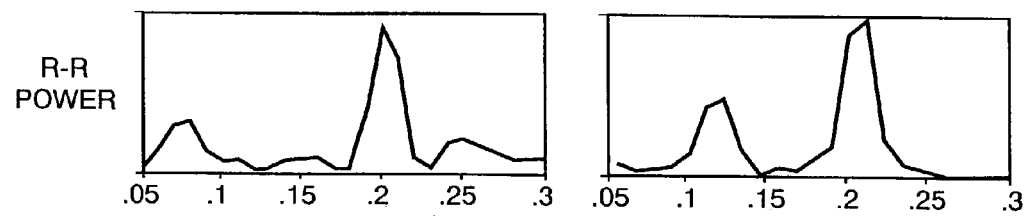
Figure 9C:
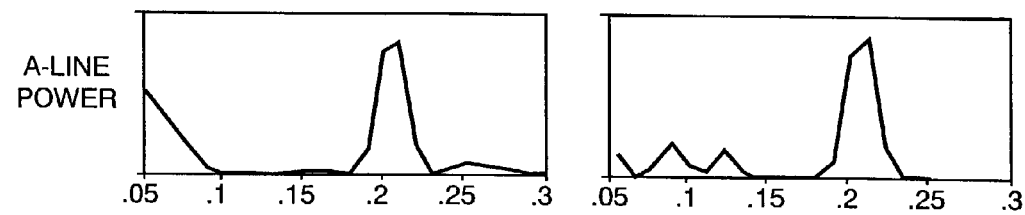
Figure 9D:
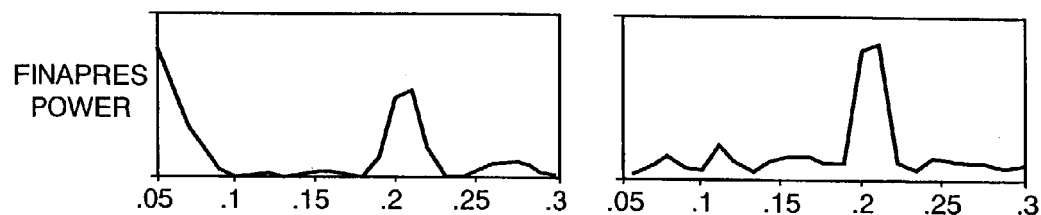
Figure 9E:
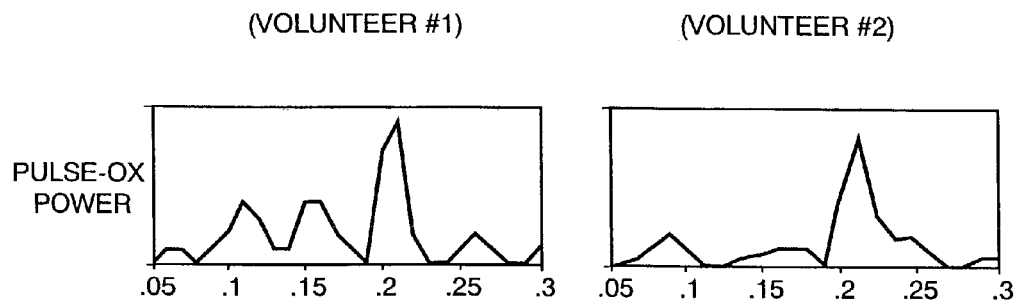
Figure 9F:
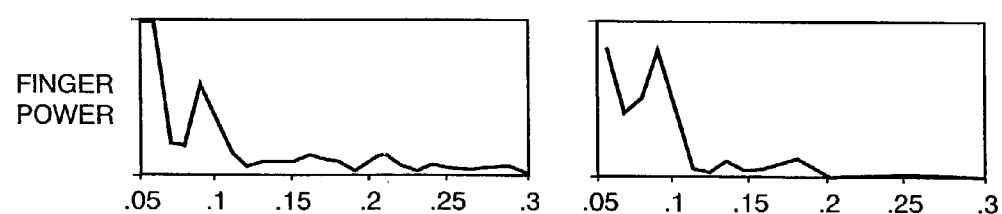
Figure 9G:
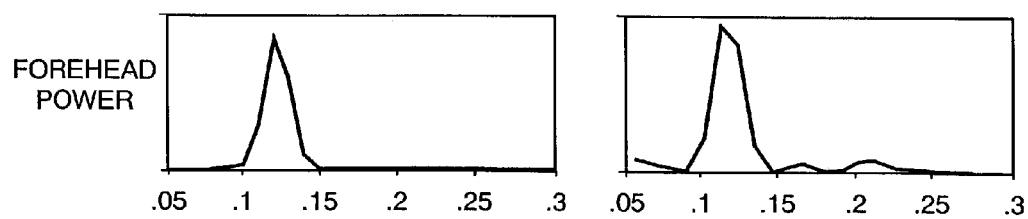
Figure 9H:
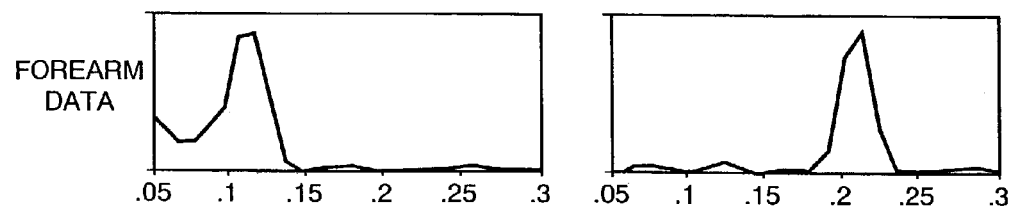

The present inventors have determined that it is possible to monitor the parasympathetic branch of the autonomic nervous system by monitoring oscillatory activity in the peripheral microvasculature of a subject. That the oscillatory activity in the peripheral microvasculature is under the control of the parasympathetic nervous system (or similarly composed fibers which release acetylcholine) is shown by three lines of evidence. First, the frequency at which power is observed in an APSD is approximately 0.12 to 0.18 Hz. This frequency is too high to be attributed to other causes of vasoregulation in the peripheral vasculature. Sympathetic pathways transmit HF impulses to the peripheral vasculature, but their complex second-messenger and reuptake systems at neuroeffector sites do not effectively generate microcirculatory oscillations at >0.12 Hz; local acid-base, hormonal, and myogenic activity induce even more protracted, LF<0.12 Hz responses (Rosenbaum M, Race D: Frequency-response characteristics of vascular resistance vessels. Am J Physiol 1968;215:1397-1402; Warner H R, Cox A: A mathematical model of heart rate control by sympathetic and vagus efferent information. J Appl Physiol 1962; 17:349-55; Pomeranz B, Macaulay R J B, Caudill M A, Kutz I, Adam D, Gordon D, Kilborn K M, Barger A C, Shannon D C, Cohen R J, Benson H: Assessment of autonomic function in humans by heart rate spectral analysis. Am J Physiol 248:H151 -H153, 1985; Pagani M, 1986; Bernardi L, Rossi M, Fratino P, Finardi G, Mevio E, Orlandi C: Relationship between phasic changes in human skin blood flow and autonomic tone. Microvasc Res 37:16-27, 1989; Bernardi L, 1997; Salerud E G, Tenland T, Nilsson GE, Oberg P A: Rhythmical variations in human skin blood flow. Int J Microcirc Clin Exp 2:91-102, 1983; Lossius K, 1995; Smith N T, 1983; Yasuda Y, Yoshizawa M, Nishino H: Effect of exercise intensity on the spectral properties of skin blood flow. Jpn J Physiol 1994;44(5):533-546; Smits T M, 1987; Preiss G, Polosa C: Patterns of sympathetic neuron activity associated with Mayer waves. Am J Physiol 1974; 226:724-30; Oude Vrielink H H E, Slaaf D W, Tangelder G J, Weijmer-Van Velzen S, Reneman R R: Analysis of vasomotion waveform changes during pressure reduction and adenosine application. Am J Physiol 1990;258:H29-37; Akselrod S, 1985; Saul J P, Dea R F, Eckberg D L, Berger R D, Cohen R J: Heart rate and muscle sympathetic nerve variability during reflex changes of autonomic activity. Am J Physiol 1990;258:H713-H721; Akselrod S, Gordon D, Ubel F A, Hannon D C, Barger A C, Cohen R J: Power spectrum analysis of heart rate fluctuation: a quantitative probe of beat-to-beat cardiovascular control. Science 213: 220-222, 1981; Chess G F, Calaresu F R: Frequency response model of vagal control of heart rate in the cat. Am J Physiol 220:554-557, 1971). Second, the activity is stimulated by agents known to stimulate parasympathetic response, for example, phenylephrine. Finally, the activity is reduced or eliminated by agents known to have the effect of suppressing parasympathetic activity, for example, atropine. As shown in FIG. 5d, the oscillatory activity described herein has a frequency of about 0.14 Hz in the $APSD_{FOREHEAD\ FLUX}$ and is stimulated by the addition of phenylephrine (compare the light trace (baseline) to the dark trace (phenylephrine)). In addition, as can be seen in FIGS. 6 and 7, the oscillatory signal is nearly eliminated by atropine. That this activity is controlled in the periphery is demonstrated by the ability to ablate the activity in one peripheral area by the application of the topical local anesthetic EMLA® (eutectic mixture of local anesthetic) without affecting the activity at a different peripheral location not treated with the local anesthetic.

An important advantage of the oscillatory signal in the peripheral vasculature as compared to other signals that can be used to determine parasympathetic activity is the relatively low value of the activity in the absence of parasympathetic stimulation as compared to the value determined in the presence of the stimulation. By way of comparison, the parasympathetic component of the R-R signal is quite substantial even in the absence of stimulation (see FIG. 5b). This high baseline value makes it difficult to detect small changes in the parasympathetic activity using the R-R signal. In contrast, the present invention utilizes a signal that has relatively little parasympathetic activity in the absence of stimulation (see FIG. 5d). This permits detection of small changes in the parasympathetic activity that were previously undetectable. The tightness of $COC_{micvasc}$ induced regulation of microcirculatory oscillatory activity in response to a vasoconstrictive challenge was most clearly evident when individual frequency bins (FIG. 6), particularly maxbins (FIG. 7)) in the $APSD_{FOREHEADFLUX}$ were assessed. For example, the 0.12 to 0.18 Hz frequency band may be broken into 6 bins, each of which has a frequency width of about 0.01 Hz. The 0.01 Hz bin with the greatest power is referred to as the maxbin. Monitoring $COC_{micvasc}$ in this manner isolated the peripheral homeostatic responses to a vasoconstrictive stimulus from the effects of respiration, a periodic perturbation with a dominant influence on HR, BP, and systemic flow that may overshadow the oscillatory effects of other changes in parasympathetic tone (FIG. 9). The observation that $COC_{micvasc}$ was more sensitive than cholinergic oscillatory control of HR ($COC_{HR}$) to a vasoconstrictive challenge was attributable, in part, to this distinction; and it is consistent with reports that HR variability is relatively insensitive to phenylephrine administration (Goldberger J J: Sympathovagal balance: how should we measure it? Am J Physiol 1999;276:H1273-H1280; Saul J P, 1990; Keys A, Violante A: The cardio-circulatory effects in man of neo-synephrin. J Clin Invest 20:1-12, 1941), that baroreceptor-associated changes in HR and BP are regulated by distinct mechanisms (Butler G C, Yamamoto Y, Hughson R L: Fractal nature of short-term systolic BP and HR variability during lower body negative pressure. Am J Physiol 267:R6-R33, 1994), and that peripheral resistance is more sensitive than HR to baroreceptor activation (Johnson J M, Rowell L B, Niederberger M, Eisman M M: Human splanchnic and forearm vasoconstrictor responses to reductions of right atrial and aortic pressures. Circ Res 34:515-524, 1974; Bagshaw R J, Cox R H: Baroreceptor control of regional haemodynamics during halothane anesthesia in the dog. Br J Anaesth 1977;49:535-544).

In one embodiment, oscillatory signals in the peripheral vasculature are used to determine parasympathetic activity, by evaluating the signals when a subject is in a baseline state, when the subject is exposed to a stimulation, and after administration of an agent known to suppress parasympathetic activity, for example, atropine. To facilitate comparison, power signals corresponding to each of the phases are broken down into frequency bins (e.g., 0.01 Hz bins). The power in each bin may be normalized by determining the average power across all bins under baseline conditions and dividing the value in each bin by this average value. Typically, the normalized power in the bin with the maximum amount of power in the stimulated subject will contain from about 500% to about 15,000% of the average power/bin in the same bin under baseline conditions. When the normalized power in the bin having maximum power in the stimulated subject fails to exceed the average power/bin or power under baseline conditions by a predetermined amount (e.g., by at least 500% or 2000%) this result is indicative of an abnormal absence of parasympathetic activity and may correspond, for example, to a patient having diabetic autonomic neuropathy. When the normalized power in the bin having maximum power exceeds the power under baseline conditions by more than a predetermined amount (e.g., by more than 13,000% or 15,000%), this result is also indicative of an abnormal autonomic nervous system and may correspond, for example, to the presence of a previously undetected vasoconstrictive state or vasoconstrictive challenge. An increased level at baseline may identify a pre-hypertensive state; an altered response to a known challenge likewise may signal a form of hypertension. Those skilled in the art will appreciate that the amount of stimulation seen in any individual instance can be affected by the nature of the stimulation used as well as by the amount and/or rate at which the stimulation is applied, and that the thresholds used to evaluate a subject's parasympathetic behavior will vary based on the stimulation used. The large stimulation seen over a low baseline value results in a very favorable signal-to-noise ratio in measurements of this activity.

Determination of the oscillatory activity described by the present inventors will be extremely useful for diagnostic purposes. For example, if a signal is seen in the absence of exogenous stimulation (e.g., normalized power in the bin having maximum power exceeds normalized average power across all bins), this may be used to diagnose one or more pathological conditions of a subject such as pre-hypertension, anxiety, drug use, pheochromocytoma, pain and/or hormonal changes associated with menopause. The failure to observe an increase in the signal when a stimulus is administered may be used to diagnose the loss of parasympathetic activity seen in various pathologies such as hypertension, diabetic neuropathy, and endothelial injury.

Figure 4A:
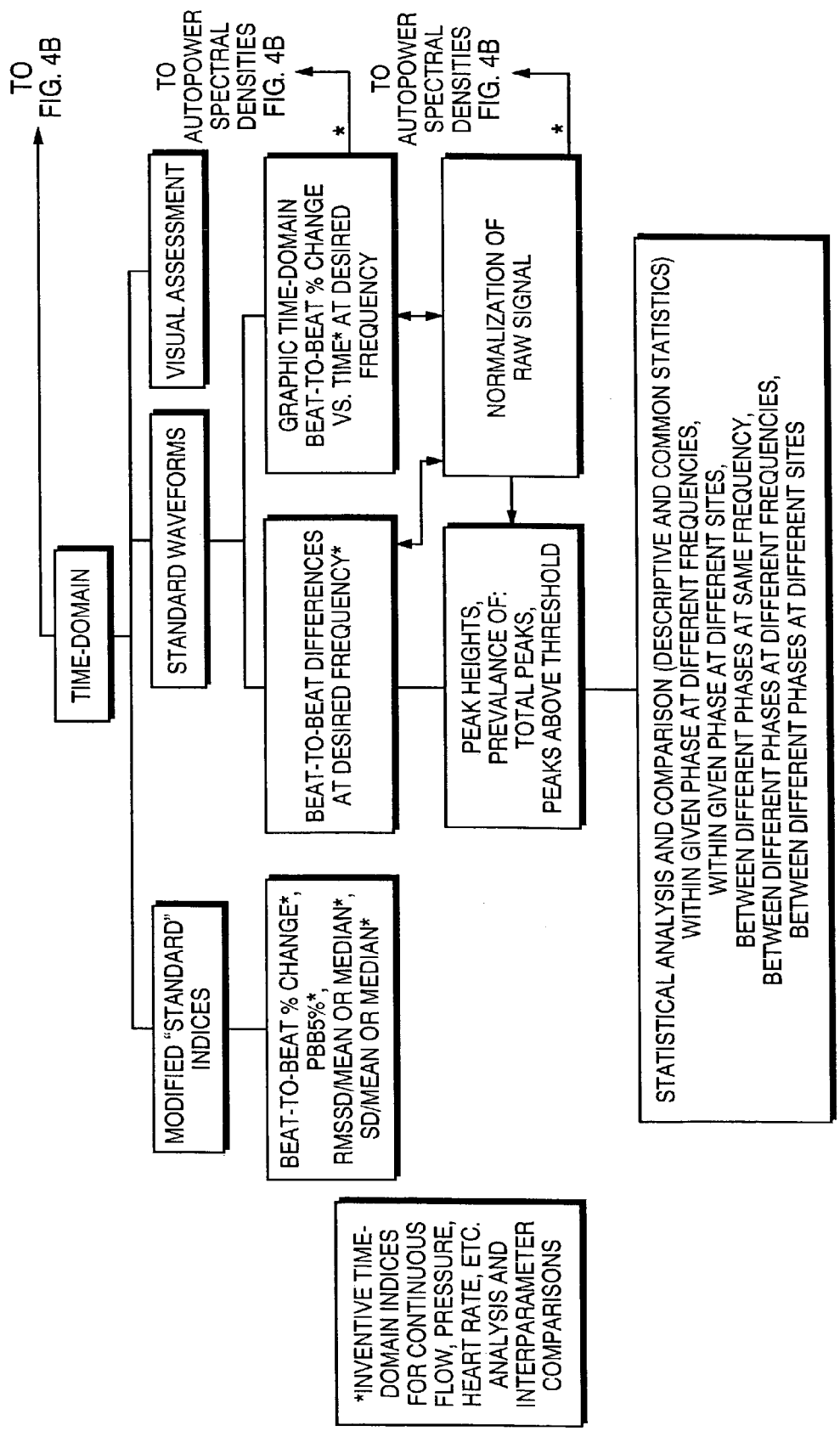
FIGS. 4A, 4B are a block diagram showing methods for assessment of biological waveforms to identify and compare oscillations at specific frequencies, in accordance with the present invention. This drawing illustrates the use of laser Doppler flux (LDF) waveforms to determine $COC_{micvasc}$. It also applies to the assessment of other biological waveforms including BP waveforms, HR and R-R tachograms, and other flow waveforms.
Figure 4B:
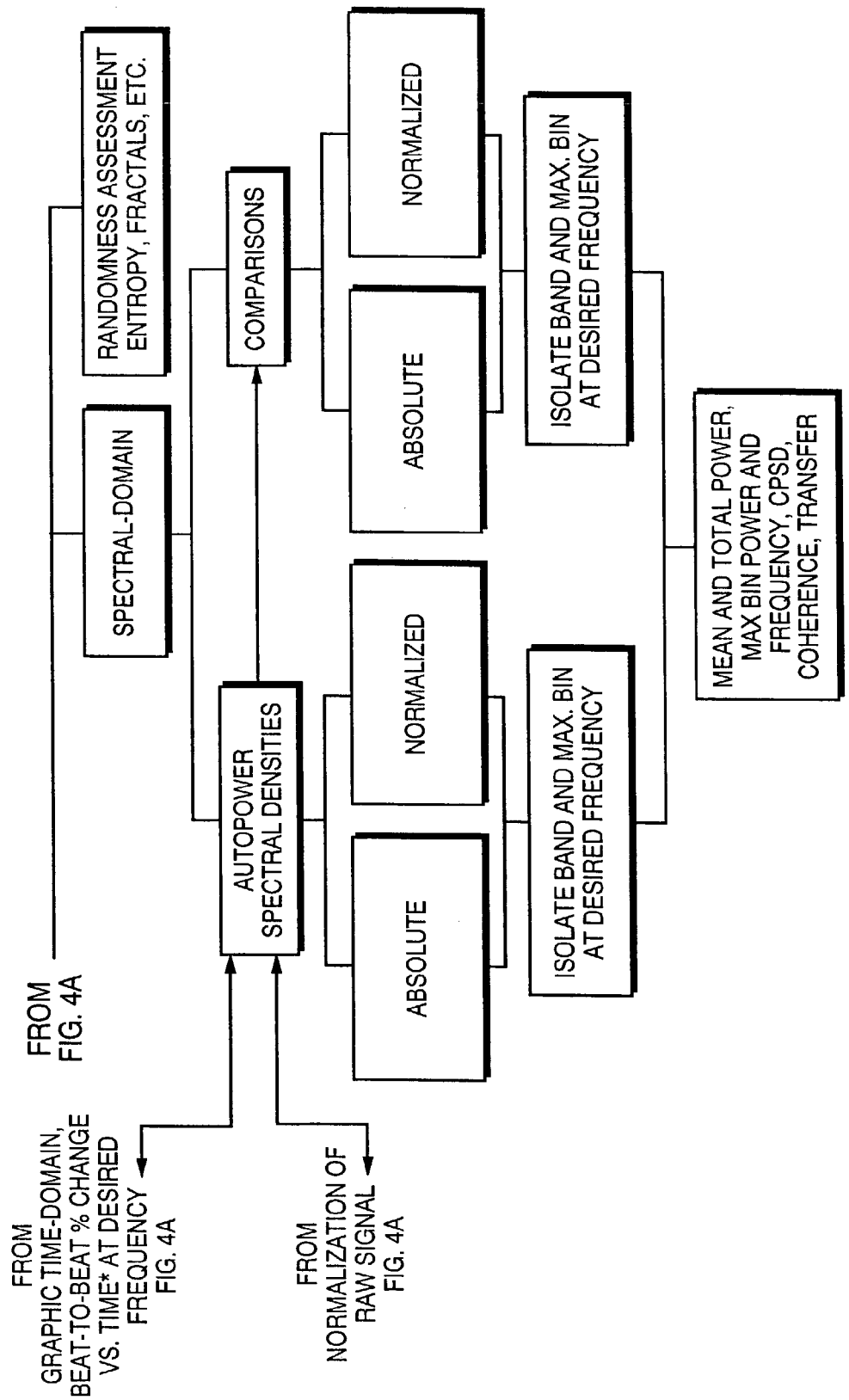

Various further features of this invention are illustrated in FIG. 4, including;

1) an inventive time-domain index which relates the incidence with which a given index changes by greater than or equal to a certain percentage (rather than by a fixed value, e.g. 50 msec of the prior art) so as to facilitate comparisons of parameters with different units of measurement and of parameters or phases with markedly different values and for establishment of relevant cutoffs;
2) other inventive time-domain indices which entail normalization of the index for a given parameter to a value such as the mean or median for that value so as to facilitate comparisons of parameters with different units of measurement and of parameters or phases with markedly different values and for establishment of cutoff values for assessment of variability;
3) assessment of waveforms for oscillations at a specified frequency or within a specified frequency range; normalization of oscillatory signals by normalizing the values of the raw signal itself to an absolute value of said signal (e.g., the mean or median) and establishment of thresholds for assessment of variability;
4) normalization by graphing the data as beat-to-beat % change vs. time and establishment of cutoffs for assessment of variability in one or more signals;
5) isolation of power at a specified frequency or within a specified frequency range as by spectral-domain analysis of the raw waveform (wherein the inventive process entails the isolation of power at the desired frequency or frequencies);
6) isolation of power at a specified frequency or within a specified frequency range as by spectral-domain analysis of the waveforms normalized by one of the aforementioned processes;
7) isolation of oscillations and oscillatory power at a specified frequency or within a specific frequency range and subsequent normalization to other frequencies, to oscillations at other sites, at other phases, and in response to other challenges
8) determination of "maxbin" by determining the frequency bin with the greatest power—typically this would be a 0.01-0.02 Hz-wide bin which may represent the maximum resolution of the APSD or constitute the sum of adjacent narrower bins (e.g., the sum of two adjacent 0.005 Hz-bins if the APSD has a resolution of 0.005 Hz).
9) means of improving temporal resolution with graphic beat-to-beat % change displays and joint time-frequency analysis.

EXAMPLE 1

Data Acquisition and Analysis

With IRB approval, 15 healthy nonsmoking male volunteers were instructed to refrain from caffeine and other known vasoactive compounds for at least 24 hours prior and then lie recumbent in a temperature-regulated room (70±1° F.). Surface electrodes were applied for monitoring ECG and respiration, a noninvasive BP cuff was placed over the brachial artery of one arm, and a 22 gauge intravenous catheter was placed in the opposite arm. In the first eight subjects, laser Doppler flowmetry probes (Periflux 2B, Perimed, Sweden) then were applied to the skin via double-stick tape on the forehead and on the finger contralateral to the BP cuff. In the remaining seven subjects, the sites of laser Doppler monitoring were modified and additional monitors were applied (see Example 3).

The ECG, respiration, and laser Doppler flux were recorded at 250 Hz with a microprocessor-based system which consisted of analog to digital converters, commercially available data acquisition and waveform analysis software (SnapMaster, HEM Data Corp.) and customized software for beat detection. Each R-wave was identified using the recommended combination of derivative plus threshold detection of the fiducial point of the data sampled at 250 Hz (Task Force of the European Society of Cardiology and the North American Society of Pacing and Electrophysiology: Heart rate variability. Standards of measurement, physiological interpretation, and clinical use. Circulation 1996;93:1043-1065). Ectopic beats were to be replaced with an interpolated value, but none were noted. BP was recorded at 2-5 min intervals.

Following 5 min of baseline (BASE) monitoring during spontaneous ventilation $BASE_{SPONT}$), each subject breathed in synchrony with an audible metronome at a rate of 12 breaths/min ($BASE_{METRO}$); each segment lasted 5 min (of which the middle 200 sec were used for subsequent analysis). Subjects then received an infusion of phenylephrine, which was titrated until there was >25% decline in finger flow for 10 min. This was achieved at between 0.4-0.6 µg/kg/min in all subjects. Five minutes of data during this PHENYL phase were recorded during SPONT and during METRO ($PHENYL_{SPONT}$ and $PHENYL_{METRO}$). Atropine was then administered IV in 0.25-0.50 mg increments until HR was at least 33% above PHENYL. Measurements during this PH+ATR phase were recorded for 5 min during each of the two respiratory patterns (PH+ATR$_{SPONT}$ and PH+ATR$_{METRO}$). The phenylephrine then was discontinued. The values from all subjects were averaged to provide the overall means±standard error (SE) for the sampling periods that are summarized in the FIGS. 5-8.

The frequency and power of the oscillations of the R-R intervals and laser Doppler flux values (flux) were characterized by frequency-domain analysis. As described in the prior art (Task Force of the European Society of Cardiology, 1996), the "R-R tachogram" and laser Doppler signal were resampled at 5 Hz, a rate more than sufficient to enable identification of oscillatory frequencies within the frequency range of interest (according to Nyquist's theorem and recent Task Force recommendations (see Task Force of the European Society of Cardiology, 1996)). An APSD was then generated for the R-R interval [APSD$_{R-R}$ (msec$^2$/Hz vs. Hz)], for the laser Doppler signal taken at the forehead [APSD$_{FOREHEAD\ FLUX}$ (mVolt$^2$/Hz vs. Hz)], and for the laser Doppler signal taken at the finger [APSD$_{FINGER}$ (mvolt$^2$/Hz vs. Hz)] in each subject using a traditional (Parzan) window. For each APSD, 200 sec of data were resampled at 5 Hz, providing a spectral resolution of 0.005 Hz (5 cycles per sec/1,000 data points); the mean value of the signal was subtracted from the data to eliminate its influence on the APSD. For purposes of presentation, each pair of adjacent 0.005 Hz bins was summated to provide bins with a width of 0.01 Hz. The power of each 0.01 Hz bin was expressed in absolute (units$^2$/Hz) and normalized (n.u.) units (relative to the average power/0.01 Hz bin at BASE during the same respiratory pattern), so as to gain the potential advantages of absolute and relative assessments.

Each APSD was initially separated into traditional LF (0.05-0.11 Hz) and HF (0.12-0.30 Hz) bands. The HF band was then subdivided into IF (intermediate frequency, 0.12-0.18 Hz) and RF (respiratory frequency, 0.18-0.30 Hz) bands; higher frequencies were excluded so as to facilitate display. In addition, for each band during each phase in each subject, the 0.01 Hz bin with the greatest power was determined by summating the power in the two consecutive 0.005 Hz bins with the highest total power. As above, the power in the max 0.01 Hz bin was normalized to the average power/0.01 Hz bin at BASE.

The interphase changes (BASE vs. PHENYL vs. PH+ATR) for each parameter of each monitor during each respiratory pattern were analyzed using paired t-test. The inter-parameter differences (e.g., APSD$_{R-R}$ vs. APSD$_{FOREHEAD\ FLUX}$) were also compared with paired t-test. As suggested by Bigger J T Jr, Fleiss J L, Steinman R C, Rolnitzky L M, Kleiger R E, Rottman J N: Correlations among time and frequency domain measures of heart period variability two weeks after acute myocardial infarction. Am J Cardiol 1992;69:891-8; and Bernardi L, 1996, if the skewness coefficient was >1.00 in one or more of the data sets for a given analysis (as was the case for each variable), the variable was considered to be significantly skewed and it was subjected to natural logarithmic (ln) transformation before t-testing.

The infusion of phenylephrine caused the anticipated increase in BP and slowing of HR (prolongation of R-R) under both spontaneous and metronome breathing conditions. The addition of atropine exacerbated the increase in BP and reversed the prolongation of the R-R interval.

Monitoring at the two laser Doppler sites identified marked differences in the responses at the finger and forehead. Finger flux declined by approximately 50% during PHENYL during both METRO and SPONT (p<0.05). In contrast, flux at the forehead remained at near-BASE values: 2.1 (0.5) at BASE$_{METRO}$ and 2.3 (0.6) volts during PHENYL$_{METRO}$ (p>0.4); 2.1 (0.5) and 1.5 (0.6) at BASE$_{SPONT}$ and PHENYL$_{SPONT}$ (p>0.3). Moreover, as detailed below, the increase in oscillatory activity at the forehead far exceeded that at the finger as well as that of R-R.

As shown in FIG. 5, the power of APSD$_{R-R}$ was primarily at the respiratory frequency (0.2 Hz). FIG. 5A shows the pseudo-continuous R-R values (sampled and graphed at 5 Hz) in the time domain. FIG. 5B is the APSD$_{R-R}$ of the entire 200-sec segment from the same subject as in FIG. 5A. Phenylephrine consistently induced a prolongation of the R-R in each subject (i.e., a slowing of HR), but it did not consistently affect the oscillatory patterns or associated power in the APSD$_{R-R}$. Oscillations at the respiratory frequency (0.2 Hz) were noted both at BASE$_{METRO}$ and PHENYL$_{METRO}$ and a prominent peak was noted at 0.2 Hz in the APSD; this response to ventilation disappeared in response to atropine (shown in FIGS. 6 and 7). FIGS. 5C and 5D present forehead flux data from the same subject as in FIGS. 5A and 5B. Phenylephrine consistently induced a more organized signal and thus caused a prominent peak in the IF band of the APSD$_{FOREHEAD\ FLUX}$. FIG. 6 shows a 3-dimensional display of power/bin during BASE$_{METRO}$, PHENYL$_{METRO}$, and PH+ATR$_{METRO}$ normalized to mean power/bin at BASE, with normalized power of R-R on left and power of forehead flux on right of each 0.01 Hz-wide bin.

The power/bin for each of the 26 bins in the APSD$_{R-R}$ during METRO averaged 475.4 (111.7) msec$^2$/Hz at BASE and only 393.8 (100.9) msec$^2$/Hz during PHENYL. IF and RF power did not increase consistently or significantly. The power of the max bin of the RF band averaged 4,354 (1556.0) msec$^2$/Hz at BASE and 4060.2 (996.2) msec$^2$/Hz during PHENYL. The normalized power of the max bin, which remained at 0.2 Hz, averaged 799.7 (138.2)% and 1050.0 (205.8)% at BASE and PHENYL, respectively.

As for METRO, there were no significant changes in spectral-domain indices during SPONT. The R-R intervals oscillated around a stable mean value with a period between 4 and 6 sec, which corresponded to the range of respiratory rates. During SPONT as well as METRO, atropine caused the power in the max bin to decrease significantly below BASE values.

The primary response of the forehead consisted of a more organized and accentuated oscillatory activity at a frequency that was distinct from that of the R-R. Power/bin of the APSD$_{FOREHEADFLUX}$ averaged 1.3(0.5) mvolt$^2$/Hz at BASE and 6.5(2.2) mvolt$^2$/Hz during PHENYL (p=0.0005). In each subject, a narrow bin within the IF band was primarily responsible for the changes in the oscillatory patterns and spectral power at the forehead site. Maxbin power, which occurred at 0.14±0.02 Hz, increased from 10.2(5.5) mvolt$^2$/Hz at BASE to 101.7(39.7) mvolt$^2$/Hz during PHENYL (p=0.0003); normalized maxbin power during PHENYL was 7,304(1,630)% of average power/bin at BASE. The addition of atropine reduced power in the maxbin to near-BASE (p=NS for PH+ATR vs. BASE). As for METRO, PHENYL$_{SPONT}$ induced an atropine-sensitive peak at 0.14±0.02 Hz (p=0.03 for maxbin at PHENYL vs. BASE;); this was 8,061(4,550)% of the average power/bin at BASE.

The phenylephrine-induced increase in overall power of the APSD$_{FOREHEADFLUX}$ was relatively greater than the change in power of the APSD$_{R-R}$ (p=0.01 during PHENYL$_{METRO}$; p=0.06 during PHENYL$_{SPONT}$). The inter-parameter difference was more dramatic for maxbin (p=0.001 during PHENYL$_{METRO}$; p=0.017 during PHENYL$_{SPONT}$). The peak in the APSD$_{FOREHEADFLUX}$ was not associated with the peak in the $APSD_{R-R}$. In the $APSD_{R-R}$, the maxbin (at 0.20 Hz) generated by respiration was predominant during BASE as well as PHENYL. Conversely, maxbin power in the $APSD_{FOREHEADFLUX}$ became predominant at a distinct frequency (at 0.14±0.02 Hz) during PHENYL. The disproportionate increase of the maxbin of the $APSD_{FOREHEADFLUX}$ during the PHENYL challenge is also evident when the values are normalized to the mean power/bin at PHENYL (as opposed to at BASE) (FIG. 8).

The delineation of maxbin is an important feature of selected embodiments of the present invention. The relative power of the maxbin of the IF band of the $APSD_{FOREHEAD\ FLUX}$ during PHENYL was significantly greater than that of any bin of the $APSD_{R-R}$ and the change induced by PHENYL in the "maxbin" of the $APSD_{FOREHEAD\ FLUX}$ was significantly greater than any change in the $APSD_{R-R}$. "Maxbins" designated with an * in FIG. 7 were significantly different from every other bin during any phase of the given respiratory pattern for the given APSD.

The power spectra illustrated by FIG. 6 facilitated comparison of the $APSD_{R-R}$ and $APSD_{FOREHEADFLUX}$ indices with different units and markedly different magnitudes.

The PHENYL-induced disparity between the maxbins of the CPSD and APSD also may be demonstrated by normalization prior to spectral domain analysis used in FIGS. 11A-D, which illustrate the comparison of data based upon dividing the 5 Hz data by the respective mean and then generating the $APSD_{R-R/mean}$, $APSD_{FOREHEAD\ FLUX/mean}$, and $CPSD_{R-R\&FLUX/mean}$. Overall, the degree to which the maxbin in the IF band of the $CPSD_{FLUX\&R-R}$ reflected the power in the maxbin of the $APSD_{FOREHEADFLUX/mean}$ decreased from 32.3±10.7% at BASE to 7.0±1.8% during PHENYL (p=0.004). Conversely, the relative degree to which the maxbin in the IF band of the $APSD_{R-R/mean}$ reflected power in the maxbin of the $CPSD_{FLUX\&R-R}$ declined from 33.6±11.0% at BASE to 7.3±1.8% during PHENYL (p=0.002).

An alternative spectral-domain analysis was performed in order to eliminate the possibility that differences between the $ASPD_{R-R}$ and $APSD_{FOREHEAD\ FLUX}$ were without physiologic significance and actually might be due to comparing continuous variable flux data (sampled at 250 Hz), with pseudo-continuous variable R-R data (with the variable interval R-R "tachogram" resampled at 5 Hz to simulate a continuous signal). For this alternative analysis R-R were treated as discrete variable interval data. This method confirmed the predominance of a peak in the $APSD_{R-R}$ at 0.2 Hz during BASE and PHENYL and the emergence of a peak at 0.14±0.02 Hz in the $APSD_{FOREHEADFLUX}$ during PHENYL also was shown when, during post-hoc analysis, flux likewise was treated as discrete variable-interval data, (FIGS. 12A-D and 13A-D) with determination of b-to-b change and then beat-to-beat % change (FIGS. 12A-D). This generated the $APSD_{b-to-b\%changeR-R}$ and $APSD_{b-to-b\%changeFOREHEADFLUX}$ shown in FIGS. 13A-D. As per the method of FIGS. 11A-D, this enabled inspection of R-R and flux data on common axes and power of the same orders of magnitude in the respective APSDs.

EXAMPLE 2

Time-Domain Analysis

The transformation of data so that both R-R and flux were treated as variable-interval data on a beat-by-beat basis also permitted comparison of time-domain indices that otherwise were not readily comparable because of different magnitudes and different units (msec and volts). As described above, the beat-to-beat % change was determined in accordance with equation (2) below, and used as a means to display the data:

$$\text{beat-to-beat \% change} = [(\text{beat}_{n+1} - \text{beat}_n)/(\text{beat}_n)] \times (100) \quad (2)$$

This method and other time-domain methods confirmed that the phenylephrine-induced change in forehead flux was characterized by increased variability (FIG. 14). A standard means (discussed below) for assessing the percentage of R-R intervals that vary by more than 50 msec (pNN50) was adapted to be applicable to assessing beat-to-beat variability of the laser Doppler signal (FIG. 14).

In order to apply standard time-domain indices of variability, i. e., standard deviation (SD) and the square root mean square of successive differences (RMSSD) in interbeat intervals to the inter-parameter comparisons, the values for each index in each phase were normalized to the median or mean value for the given subject to create two indices to perform novel interparameter comparisons.

Time-Domain Assessment of R-R Variability

As noted in FIG. 14, the lack of an increase in spectral power of the $APSD_{R-R}$ was associated with a lack of significant change in time-domain indices of beat-to-beat variability. During metronome breathing, the beat-to-beat % change of R-R was 4.3 (0.6)% at BASE and 5.6 (0.7)% during PHENYL (p=0.2); during spontaneous breathing, the respective values were 3.2 (0.4)% and 3.7 (0.4)% (p=ns). For R-R, pBB5% was similar to pNN50 (p=NS for difference between these indices during BASE, PHENYL or PH+ATR). The changes in rmssd/median and SD/median are also shown in FIG. 14.

Time-Domain Assessment of Flux Variability

As shown in FIG. 14, the increase in power within the $APSD_{FLUX}$ of the forehead was associated with a significant increase in the time-domain indices of variability. During METRO, the beat-to-beat % change of forehead flux was 4.9 (1.1)% at BASE and 11.9 (2.3)% during PHENYL (p<0.05). During SPONT, the values were 3.4 (0.3)% and 10.7 (2.2)% (p<0.05). The changes in pBB5%, pBB10%, SD/median and rmSSD/median are summarized in FIG. 14.

EXAMPLE 3

Alternative Data Acquisition Configurations

The data generated by the aforementioned protocol prompted additional trials which included: 1) assessments of the response to bolus administration of phenylephrine, a challenge which typically elicits a more robust baroreceptor response than infusion but is not as amenable to prolonged testing (n=10 subjects); 2) the use of multiple forehead probes so as to determine the heterogeneity of responses among different forehead sites (n=6 subjects); 3) the topical application of a eutectic mixture of the local anesthetics lidocaine and prilocaine (EMLA, Astra) to eliminate local neural activity at one of the study sites (n=4 of the subjects monitored with multiple probes); 4) laser Doppler flowmetry of the forearm as well as the finger and forehead (n=2 subjects); and 5) continuous plethysmographic measurements of finger flow and continuous monitoring of finger arterial and radial artery BP waveforms so as to permit comparisons of the oscillatory patterns in the forehead to these additional indices (n=1 subject during infusion; n=2 subjects during bolus).

The findings in the subject who received a phenylephrine infusion during continuous intra-arterial monitoring showed that the oscillations in forehead flow occurred at a different frequency from the oscillations in systemic BP. The maxbin of the $APSD_{FOREHEAD\ FLUX}$ was at 0.13 Hz. Consistent with the well-established influence of respiration on BP variability, the BP oscillated at the respiratory frequency (0.20 Hz) during BASE as well as PHENYL. Comparable disparities were obtained in the two subjects who received phenylephrine as a bolus while being monitored at multiple sites (FIG. 9). Oscillations in the forehead increased dramatically at approximately 0.13 Hz in these two subjects. Conversely, R-R variability, continuous radial BP, continuous finger BP, finger plethysmographic, and finger flow readings did not develop the prominent increase within the IF band. As for the R-R tachogram, the BP and plethysmographic waveforms were centered at the respiratory frequency at BASE and remained centered at this frequency during PHENYL.

Figure 10B:
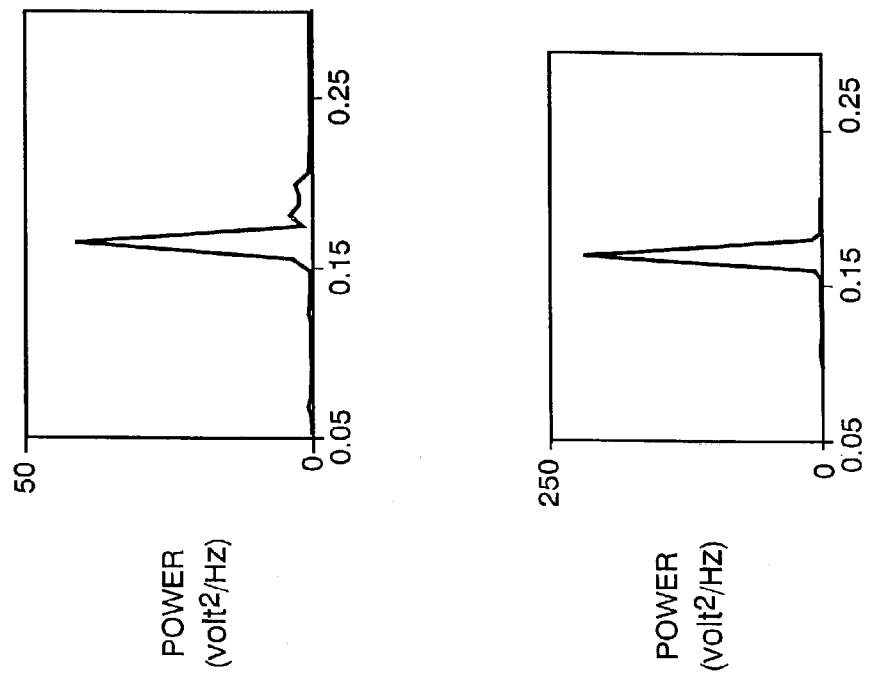
FIGS. 10A-B are a composite showing that forehead flux at different sites may oscillate out of phase even if the sites oscillate at the same frequency. These figures show data from a subject monitored with multiple forehead probes during middle 60 sec of a phenylephrine infusion during metronome breathing at 0.2 Hz.
Figure 10A:
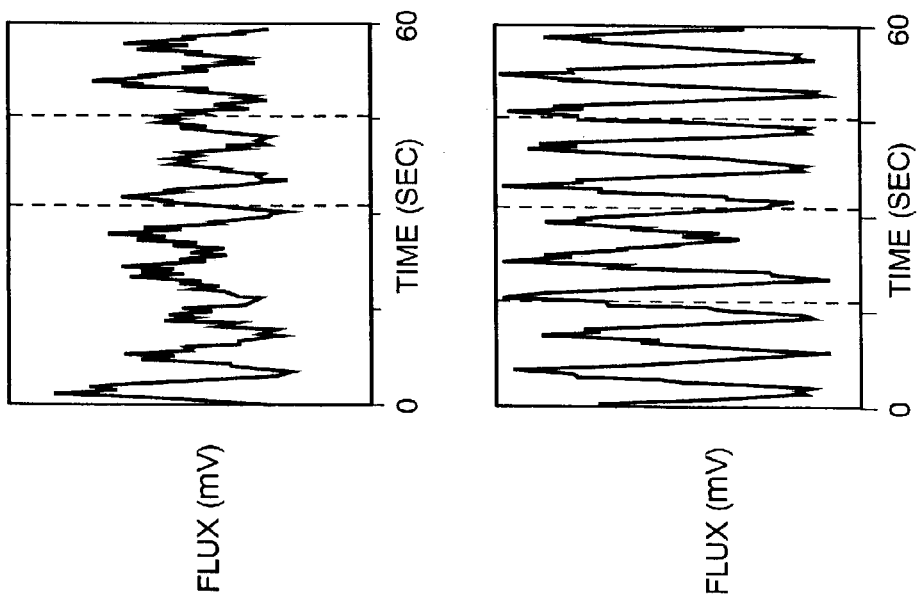
Figure 11C:
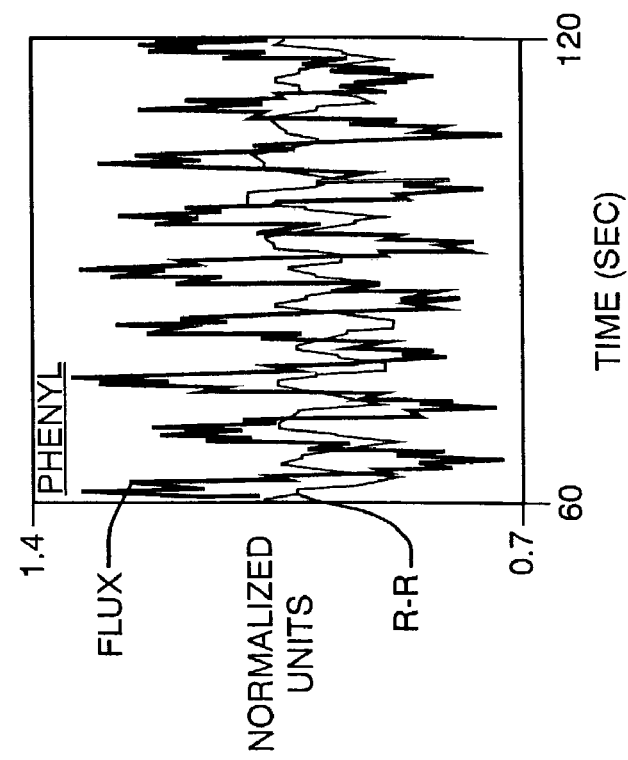
FIGS. 11A-D are a graphical comparison of normalized data in the time and frequency-domains, in accordance with the present invention. These figures compare the R-R (light line) vs. flux (dark line) waveforms for the subject shown in FIG. 5. The signals were normalized prior to time and frequency domain analysis, as follows: (1) LDF flow data was resampled at 5 Hz (data from FIG. 5); (2) mean flow data for the entire study segment (i.e., 5.33522) was determined; and (3) the normalized values were obtained by dividing each resampled value by the corresponding mean value for the study segment. Normalization facilitates visual inspection as well as time-domain and spectral-domain comparisons of the oscillatory signal(s) to values under different circumstances (e.g. baseline vs. challenge state) or to the values of another parameter. Although the values in FIG. 11 were normalized to the mean, it may be preferable in some settings to normalize to the median since this is less affected by outliers.
Figure 11A:
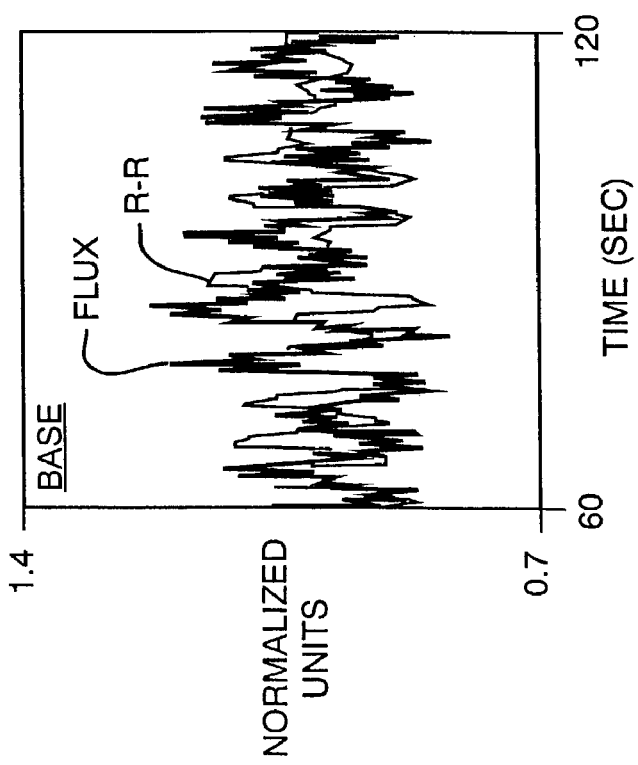
Figure 11B:
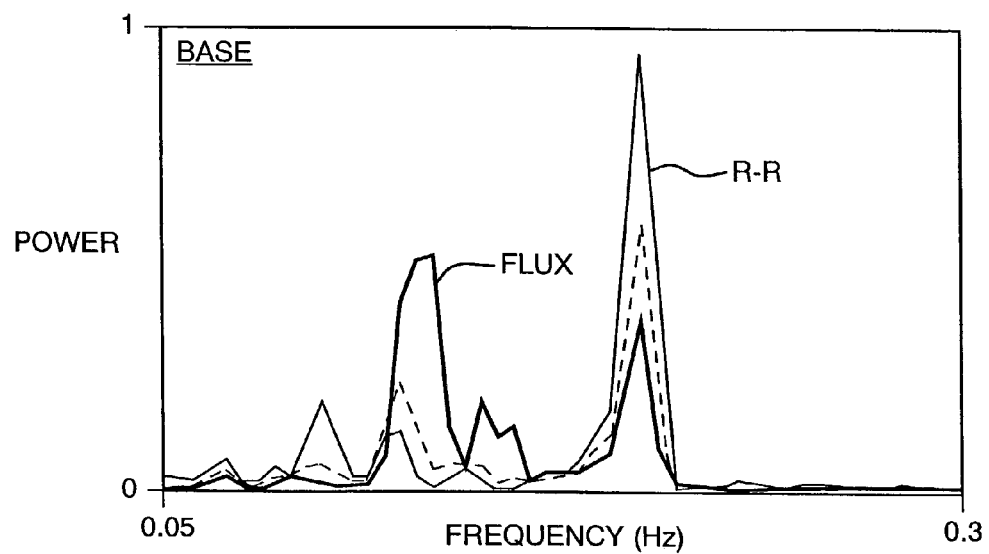
Figure 11D:
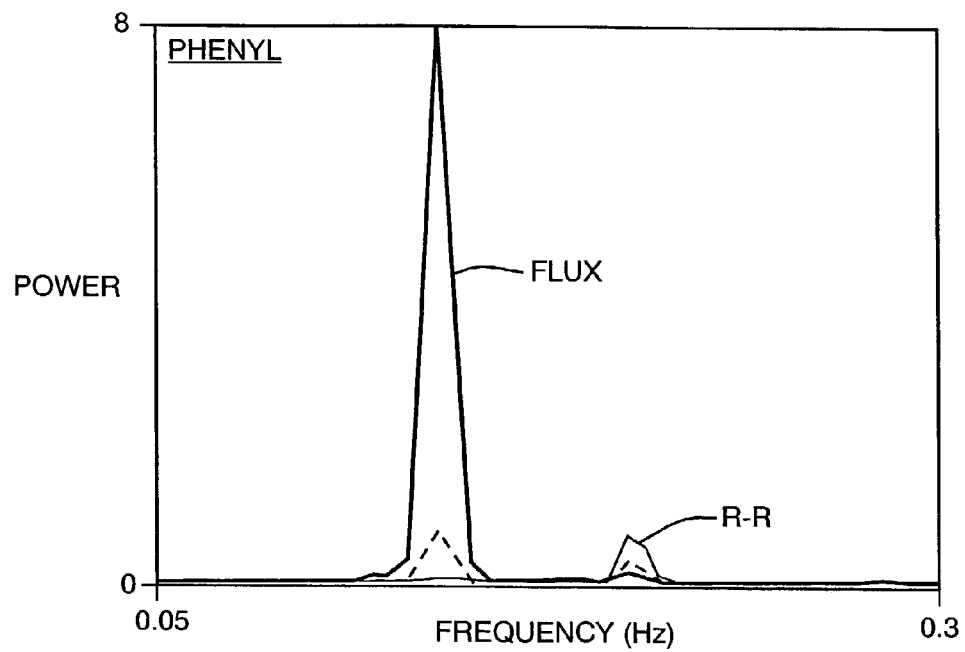
Figure 12A:
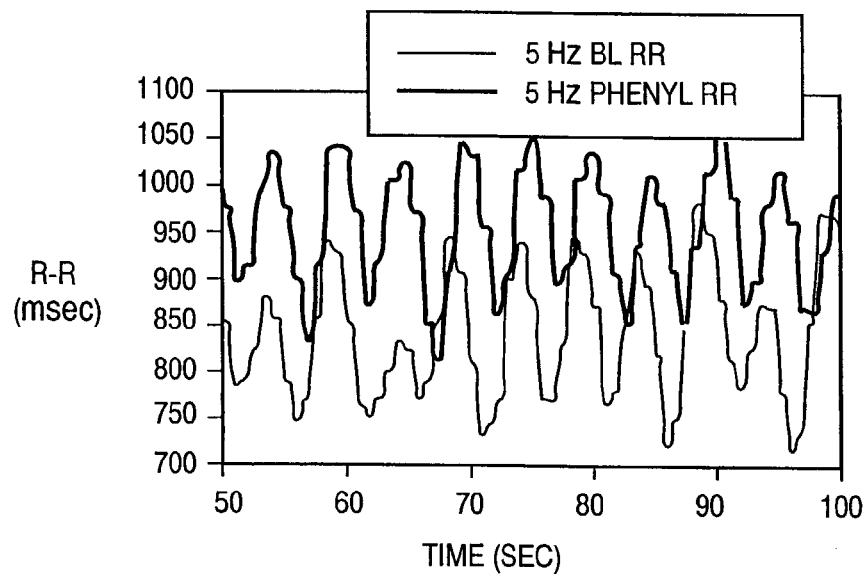
FIGS. 12A-D are a graphical comparison of normalized data in the time-domain, in accordance with the present invention. Here, the data was normalized as follows: (1) LDF flow data (data from FIG. 5) is separated on a beat-by-beat basis so that the mean value at each beat ($A_1$, $A_2$ . . . $A_n$) is shown (other values such as maximum, minimum, and maximum minus minimum could also be shown on a beat-by-beat basis); (2) the difference between the maximum values of successive beats (Flux Change, FC) is determined; and (3) the normalized values are generated by normalization of the difference to the initial value (($A_2$-$A_1$)/$A_1$ . . . ($A_n$-$A_{n-1}$)/$A_n$) (note that the difference similarly could be normalized to the mean value).
Figure 12B:
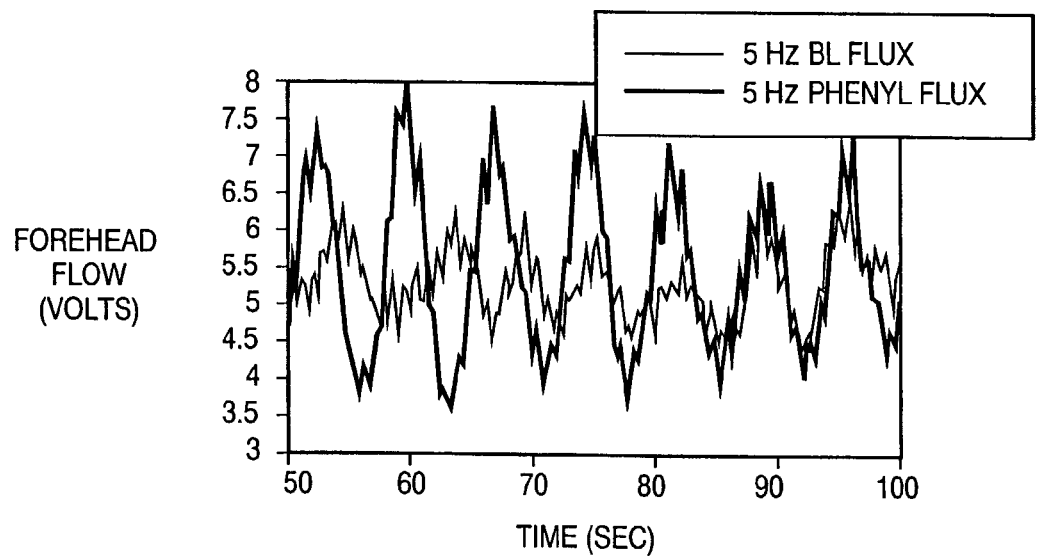
Figure 12C:
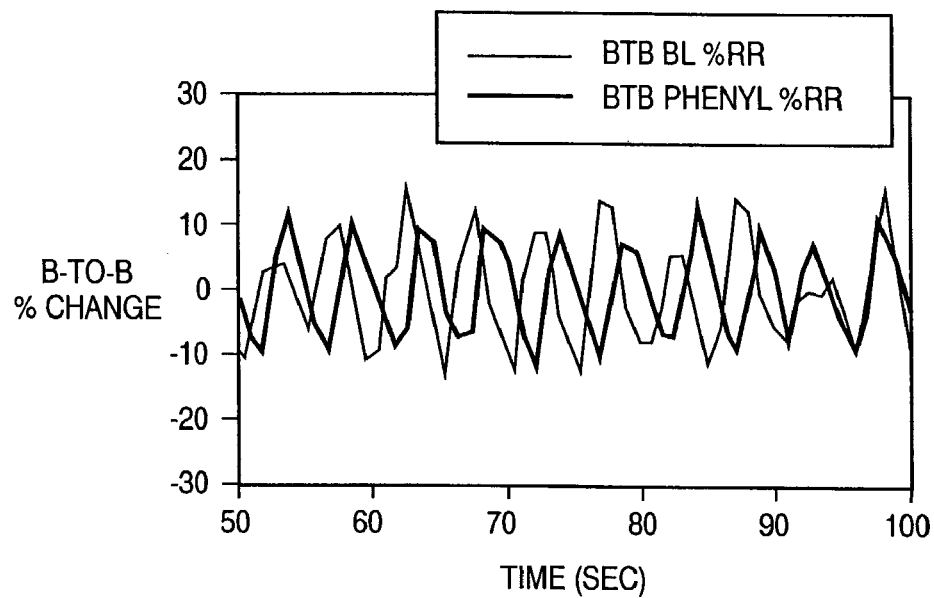
Figure 12D:
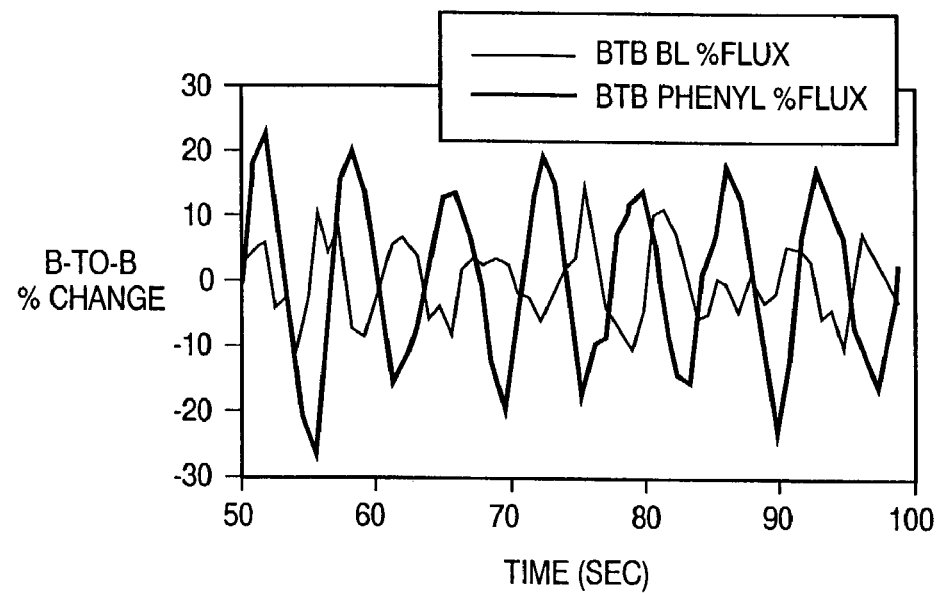
Figure 13C:
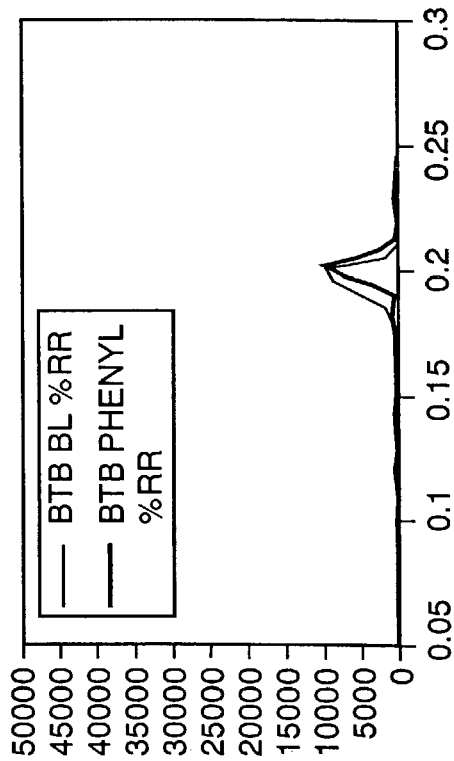
Figure 13A:
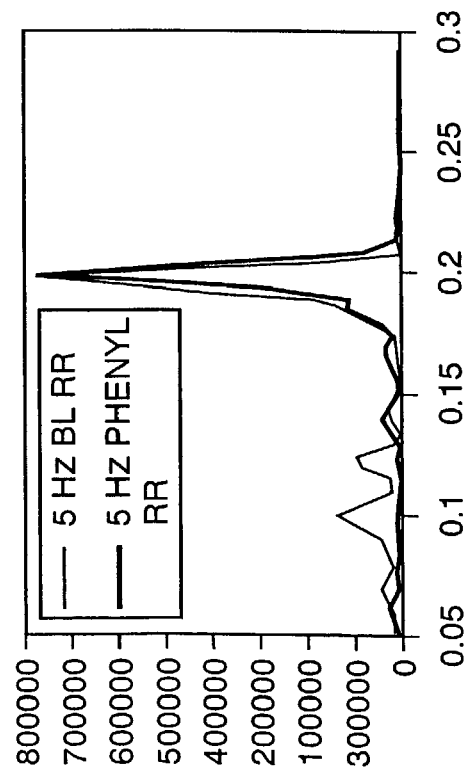
Figure 13D:
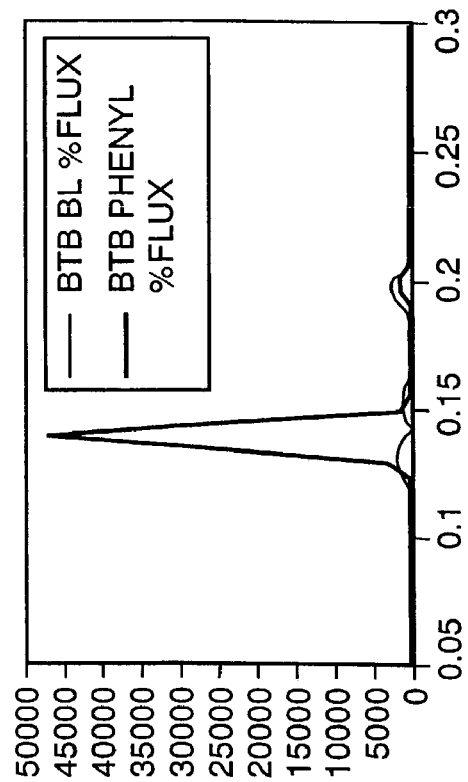
Figure 13B:
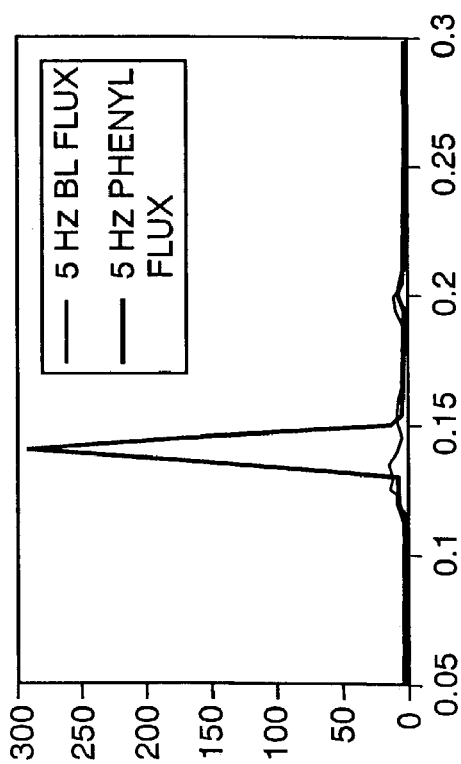

The use of multiple laser Doppler probes on the forehead (n=6 subjects) revealed that, although each site developed an increase in IF power during PHENYL, the oscillations at the different forehead sites were not necessarily in phase with one another (FIG. 10). This indicated that the oscillatory control was at the level of the local microvasculature as opposed to a more proximal location that would have synchronized the vessels under different probes.

Topical application of local anesthetic under a forehead probe eliminated phenylephrine-induced oscillations. These data, noted in the four subjects in whom EMLA was applied, constitute strong evidence that the EMLA-sensitive peak is a consequence of neural control that is mediated at the level of the peripheral vasculature, thereby confirming the peripheral mediation of the oscillatory control.

Referring now to FIGS. 9A-H, these figures represent composite data indicating that phenylephrine-induced parasympathetic activity at the forehead is not transferred from more proximal sites in the body. These Figures address whether oscillations >0.12 cycles/sec in microvascular flow during a vasoconstrictive challenge constitute a homeostatic cholinergic response at the level of the microvasculature or whether they simply represent oscillations that originate at the heart and are transmitted to passive microvascular beds. Heart rate, blood pressure, respiratory rate, and laser Doppler flowmetry of the forehead and finger were monitored in healthy volunteers at baseline, during systemic infusion of phenylephrine (0.4-0.6 µg/kg/min), and during subsequent addition of intravenous atropine ($\leq 2.0$ mg/70 kg). Spectral-domain analysis documented that atropine-sensitive oscillatory power of the R-wave to R-wave intervals of the electrocardiogram was predominant at the respiratory frequency (0.20 Hz) at baseline as well as during phenylephrine infusion. In contrast, arteriolar-capillary networks of the forehead developed a prominent atropine-sensitive oscillatory peak at 0.14±0.02 Hz during phenylephrine infusion (p<0.05 for differences in oscillatory magnitude and frequency between forehead flow and R-R intervals). The cross-power spectral density confirmed the lack of common power between forehead flow and R-R oscillations. Post-hoc assessments showed that—similar to heart rate—systemic pressure and systemic flow also had persistent power at 0.20 Hz and did not develop a peak at the forehead oscillatory frequency; phenylephrine likewise did not induce atropine-sensitive oscillations in the finger, a finding attributable to adrenergic predominance in this region. Based on this, the inventors conclude that atropine-sensitive oscillatory activity in the forehead microvasculature in response to a vasoconstrictive challenge constitutes a local response that is not due to, nor associated with, mechanical transmission from the heart and proximal vasculature.

EXAMPLE 4

Diagnosis Based Upon Peripheral Oscillatory Activity

As shown in FIG. 17, one or more leads 10 for determining an oscillatory signal may be attached to one or more regions of a subject 15. In preferred embodiments, at least one lead may be attached to a peripheral region of the subject, for example, the forehead 18. The leads may convey information on an oscillatory signal to one or more data acquisition devices 20. The data acquisition devices may be optionally connected to a display device 30 and a computer system 40, for processing and displaying data in accordance with the methods described herein.

Figure 1A:
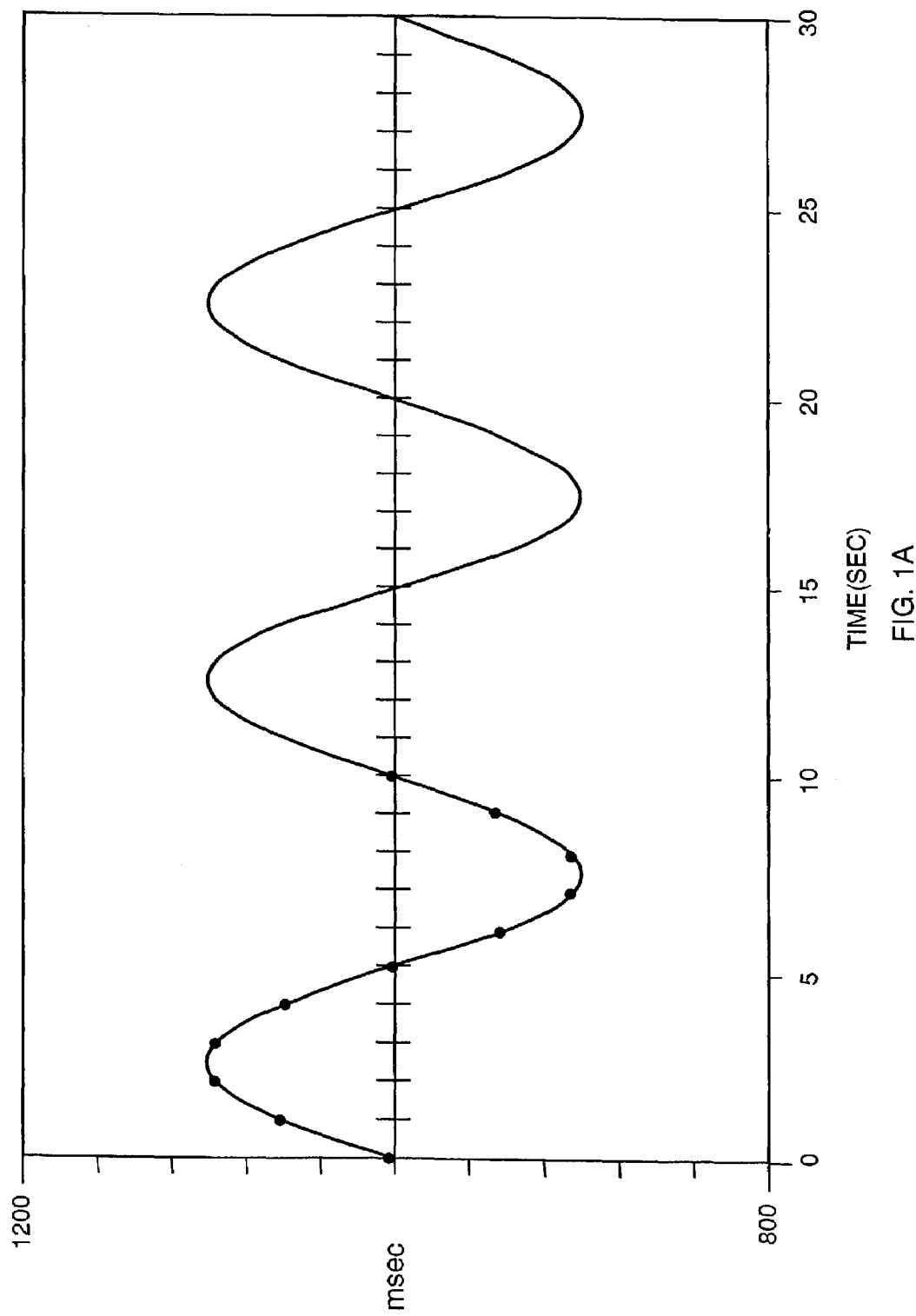
FIGS. 1A, 1B show prior art techniques for analysis of data in the time- and frequency-domains.
Figure 1B:
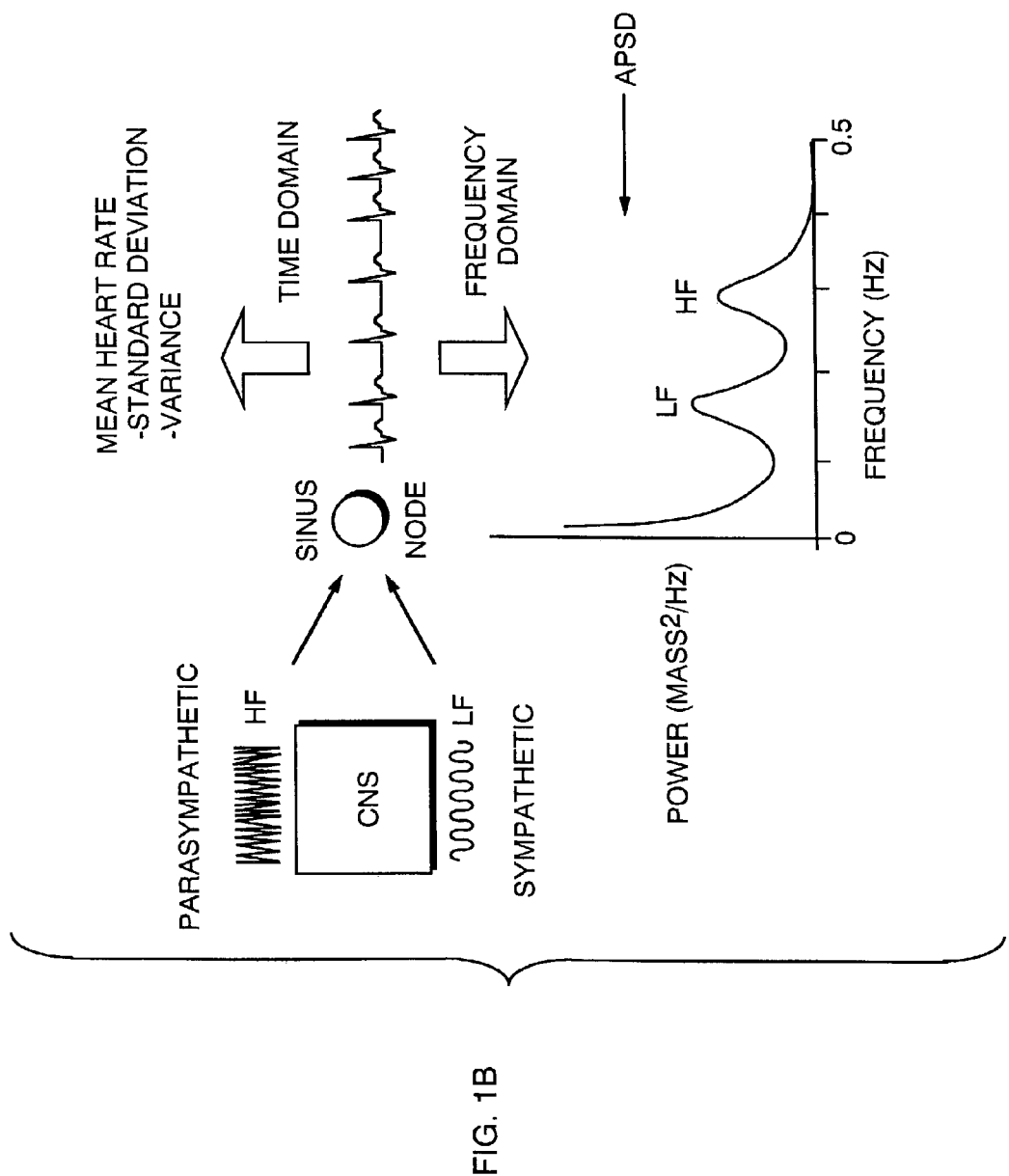
Figure 2:
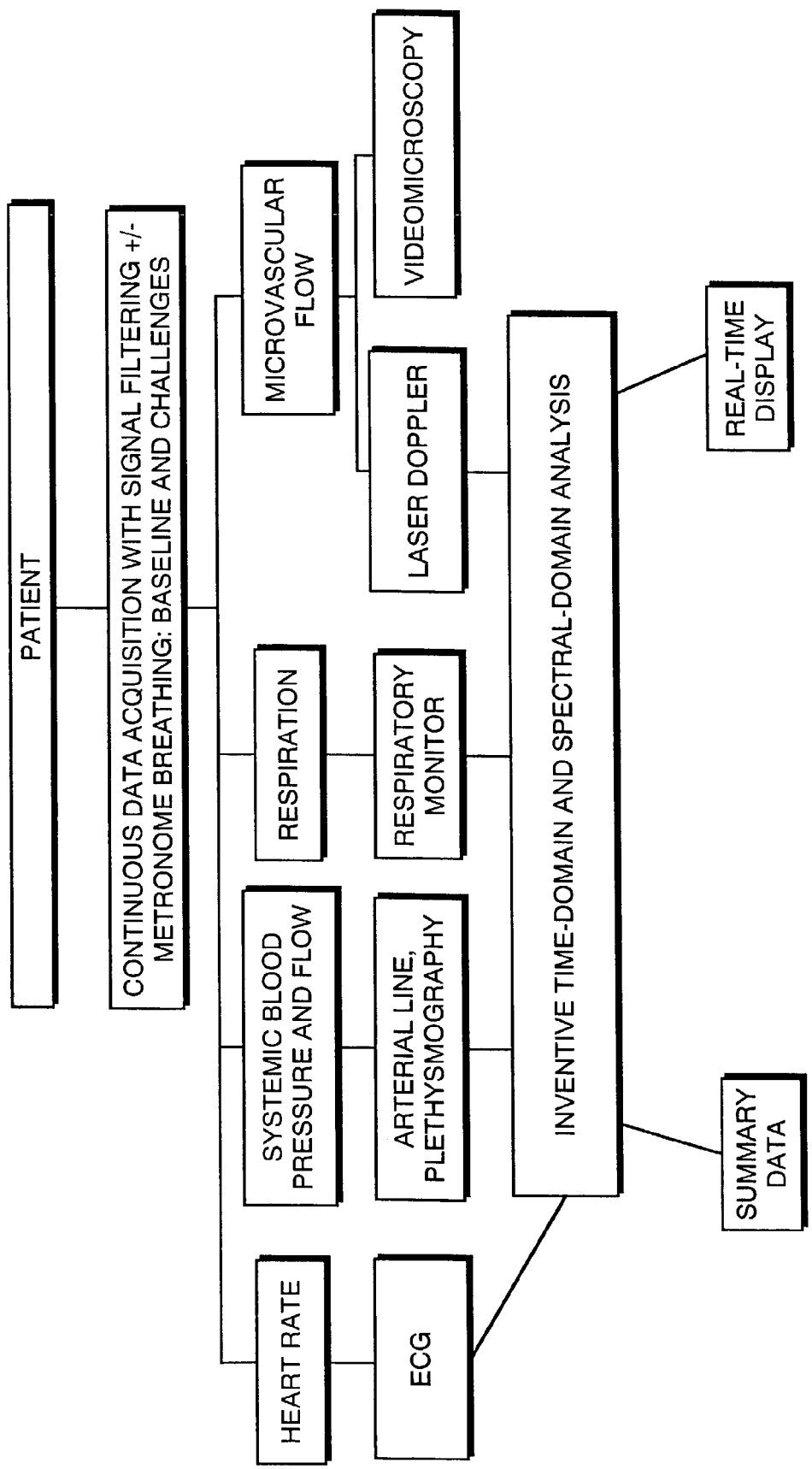
FIG. 2 is a block diagram showing methods for Measurement of Cholinergic Oscillatory Control of the microvasculature ($COCC_{micvasc}$) in accordance with the present invention. The diagram shows the data collection, signal processing, and analysis that may be applied to characterize oscillatory activity in the approximate 0.12-0.18 Hz range.

The oscillatory signal may be determined using any method known to those of skill in the art. For example, in some preferred embodiments the oscillatory signal may be determined by contacting a site adjacent the subject's peripheral microvasculature (e.g., forehead) with one or more probes that supply interrogation signals and observing one or more reflected signals. An example of this type of determination is LDF. In other embodiments, the oscillatory signal may be determined by alternative optical techniques, including techniques other than those shown in FIG. 2. Optical techniques preferably comprise the use of a magnification means such as a microscope or video camera. Such optical techniques include, but are not limited to, microscopic examination such as vital videomicroscopy of the change in diameter of the blood vessels of the subject in vivo. Other preferred embodiments include determination of the oscillatory activity of the subject using a transduced signal. Other methods of determining an oscillatory signal need not be limited light; e.g., electrical signals may be used. In embodiments of this type, the oscillatory activity may be detected with a sensor that transduces the oscillatory signal into a signal suitable for data acquisition.

In a particularly preferred embodiment, the oscillatory signal is evaluated by attachment of an LDF probe to a subject's forehead. Using LDF, an APSD of the forehead signal ($APSD_{forehead\ signal}$) (typically is the forehead flux) is obtained for a subject both during a baseline study phase and during a study phase wherein the subject is exposed to a sympathetic challenge such as, for example, the administration of a pharmacological agent (e.g., phenylephrine). The $APSD_{forehead\ signal}$ from the PHENYL study phase is then preferably normalized. This normalization may be performed, for example, by averaging the power in each 0.01 Hz wide bin in the 0.05-0.30 Hz frequency band of the $APSD_{FOREHEAD\ FLUX}$ derived during the BASE study phase, and then dividing the power in each 0.01 Hz bin in the PHENYL study phase by this average amount. Other normalization steps, as described above, could alternatively be applied. Following the normalization, the 0.01 Hz bin having the maximum power in the $APSD_{forehead\ signal}$ from the PHENYL phase is identified. The maximum power in such "maxbin" from the PHENYL phase is then compared to the normalized power in the corresponding bin from the BASE phase of the study. Thus, for example, if the normalized power in the 0.14-0.15 Hz bin from the $APSD_{forehead\ signal}$ from the PHENYL phase of the study has more power than any other 0.01 Hz bin in the $APSD_{forehead\ signal}$ from the PHENYL phase of the study, then the power from the 0.14-0.15 Hz bin in the $APSD_{forehead\ signal}$ from the PHE- NYL phase of the study will be compared to the normalized power in the 0.14-0.15 Hz bin from the $APSD_{forehead\ signal}$ from the BASE phase of the study. For purposes of nomenclature, the 0.01 Hz wide bin having maximum power in the approximate 0.12-0.18 Hz band of the $APSD_{forehead\ signal}$ from the PHENYL phase of the study shall be denoted in accordance with equation (3) as follows:

$$BIN_x = (MAXBIN(APSD_{FOREHEAD\ FLUX-PHENYL})) \quad (3)$$

Similarly, the power in this bin shall be denoted in accordance with equation (4) as follows $$Power = P(BIN_x(APSD_{FOREHEAD\ FLUX-PHENYL})) \quad (4)$$

Finally, the ratio of the power in $BIN_x$ from the PHENYL phase of the study to the power in the corresponding bin from the BASE phase of the study shall be denoted in accordance with equation (5) as follows $$RATIO = \frac{P(BIN_x(APSD_{FOREHEAD\ FLUX-PHENYL}))}{P(BIN_x(APSD_{FOREHEAD\ FLUX-base}))} \quad (5)$$

In a preferred embodiment, if the RATIO described above fails to exceed a minimum threshold, this result would be indicative of an abnormal absence of parasympathetic activity and may correspond, for example, to a patient experiencing advanced hypertension or diabetic autonomic neuropathy. In one embodiment, such a diagnosis would only occur if the RATIO failed to exceed a threshold of 2,000%. In other embodiments, such a diagnosis would result if the RATIO failed to exceed a threshold of 500%. These particular thresholds are based on the data shown, for example, in FIGS. 6, 7, and 8. These data would appear to indicate that, in normal subjects exposed to the dose of phenylephrine used in the aforementioned investigation, the RATIO may be as low as 500% or 2,000%, and that therefore, when the RATIO falls below such thresholds, such a result would be indicative of an abnormal absence of parasympathetic activity.

In addition, when the RATIO exceeds a different predetermined threshold (e.g., by more than 13,000% or 15,000%), this result may be indicative of an abnormal parasympathetic nervous system and may correspond, for example, to a subject in a pre-hypertensive state. In two prehypertensive subjects, the prehypertensive state was identified by greater than normal oscillatory power at baseline (FIGS. 16A-C).

Those skilled in the art will appreciate that the amount of stimulation seen in any individual instance will be affected by the nature of the stimulus used, as well as by the amount and/or rate at which the stimulation is applied, and that the thresholds used to evaluate a subject's parasympathetic response will therefore vary based on the stimulation used. The specific thresholds described above should therefore be viewed as exemplary thresholds used in a particular embodiment of the invention, rather than being imitative of the scope of the present invention.

Although in the above-described embodiment, the subject was exposed to a pharmacologic challenge resulting from systemic administration of phenylephrine, in other embodiments of the present invention the subject may be exposed to a different challenge in connection with determining one or more oscillatory activities. The challenge may be delivered before, during or after determining an oscillatory signal. The challenge may be invasive or non-invasive. The challenge may be a pharmacological challenge. For example, one or more pharmacological agents may be administered to the subject by any means known to those skilled in the art. In some preferred embodiments, the pharmacological challenge may comprise the administration of one or more agents having a vasoconstrictive activity. Some preferred pharmacological agents include, but are not limited to, phenylephrine (described above), levophed, and epinephrine. This may be delivered systemically or locally as by intradermal injection or iontophoresis. The physiologic challenge may be administration of a mental stress, for example, requiring the subject to do mathematical calculations. The physiologic challenge may be a change in position of the subject. For example, the subject may be tilted to an angle of from about 45° to about 90° from the vertical, a preferred angle is about 60°. The physiologic challenge may be a physical stress, such as physical effort or strenuous exercise, hyperventilation, placing the subject's hand or foot in cool water or cooling the subject's face. Other physiologic challenges that are known by those skilled in the art to have an effect on the autonomic nervous system may likewise be used, for example, the Valsalva maneuver. It is helpful to use a metronome to isolate the respiratory signal. Other methods to eliminate the influence of respirations on oscillatory activity may be used.

In still further embodiments of the present invention, an oscillatory signal may be determined from a subject at rest (i.e., in the absence of an external physiological challenge). The subject may be at rest for varying periods of time prior to the determination of the signal. In some preferred embodiments, the subject may be at rest from about 30 minutes to about 1 hour. When determining a signal from a subject at rest, it may be desirable to look for the absence of an expected activity or the presence of an activity that is not normally present. In addition, it may be desirable to look for the amount of an activity to determine whether the amount is greater or lesser than the amount of the corresponding activity in a normal subject or reference signal. For example, in one embodiment, the $APSD_{FOREHEAD\ FLUX}$ for a subject at rest (referred to hereafter as the $APSD_{foreheadrest\ signal}$) is analyzed by first determining the power in each 0.01 Hz wide bin in the approximate 0.12-0.18 Hz band of such signal, normalizing the power in each such bin by the average power across all bins in the desired range of the spectrum (often this would be 0.05-0.30 Hz), and then comparing the normalized power of the bin in the approximate 0.12-0.18 Hz band having maximum power (referred to hereafter as $BIN_x$) to a threshold. In this example, if the value of the power in $BIN_x$ exceeds the threshold, this result may be indicative that the subject is in a pre-hypertensive state or is otherwise reacting as if being stressed by a vasoconstrictive challenge. In this example, the comparison threshold against which $BIN_x$ will be compared is 1000%. Again, this threshold is supported by the data shown in FIG. 6, which demonstrates that for normal subjects, the value of $BIN_x$ (as illustrated in the BASE phase information of FIG. 6) is normally within this threshold. Such an exaggerated response at baseline led us to accurately suspect—and hence identify—a prehypertensive state in two subjects (FIG. 16).

If one uses time-domain analysis, then he/she would analyze the time-domain for briefly delimited segments such as that described for joint time-frequency analysis. Alternatively, one could examine a continuous signal or a signal modified for variable time-interval data in order to determine if oscillations in the approximate 0.12-0.28 Hz range were occurring and then measure the incidence of such activity and/or the magnitude of variability.

In some embodiments of the present invention, it may be desirable to determine an oscillatory signal from more than one portion of the subject's anatomy. The signal may be determined using the same technique in all locations of the subject's anatomy. Alternatively, at one or more of the locations, the signal may be determined using different techniques. In preferred embodiments, at least one location will be in a peripheral region of the subject. In some preferred embodiments, an oscillatory signal from the heart, for example, HR variability, may be compared to an oscillatory signal determined in the periphery of the subject, for example, in the forehead, forearm and/or finger. In some embodiments, it may be desirable to determine an oscillatory signal from a pulsatile waveform, for example, blood pressure. Blood pressure may be determined using any technique known to those skilled in the art, such as invasively via intra-arterial catheter interfaced with a transducer or indirectly via a noninvasive device which is sensitive to changes in pressure or volume such as a continuous finger arterial pressure monitor (FINAPRES) In some embodiments, an oscillatory signal may be determined from the heart using an EKG and compared to an oscillatory signal determined in the periphery using LDF.

In order to facilitate the comparison between a discrete, intermittent (variable-interval) signal such as the R-wave of the EKG and a continuous wave such as that generated by laser Doppler flowmetry, researchers and clinicians heretofore have relied on transforming the R wave-to-R wave intervals into a pseudocontinuous signal by resampling the R-R intervals at a frequency such as 5 Hz (such that the time of the R-wave for the given beat would be resampled every 0.2 sec until the time of the next beat is reached). This traditional method does not permit comparison of the different waveforms and their frequencies under identical conditions in that a pseudocontinuous wave is not equivalent to a continuous wave (as would be generated by laser Doppler flowmetry, continuous plethysmographic flowmetry, or continuous arterial pressure monitoring). We therefore have invented a means for transforming the continuous signal so that it is consistent with the intermittent R-R signal and thus can be analyzed identically. This is accomplished by segmenting the continuous data on a beat-by-beat basis after identifying each R wave in a manner well known to those experienced in the prior art. The inventive conversion to a common format entails generation of a customized spreadsheet (or equivalent) (data not provided) and determination of indices such as the maximum, minimum, max-min, and mean of each waveform for each beat.

One can then use the max, min, max-min, or mean for each beat (for purposes of this discussion, we will use the maximum) and then perform analysis consistent with those of the single value for the EKG, that being the time of the R wave. One or more of the common signals generated by this inventive process can then be assessed and/or compared on a beat-to-beat basis by time-domain analysis as well as by spectral-domain analyses. Both forms of analysis may be aided by normalization. This may be accomplished by: 1) normalization of raw data before analysis; or 2) normalization of time-domain and spectral-domain indices during or after analysis. Time-domain may focus on actual values/beat, relative values/beat, and changes in these indices. These may be used to generate summary statistics (e.g., mean+standard deviation) or real-time displays (as shown in FIG. 18). Spectral-domain analysis of the beat-by-beat data will differ from traditional spectral-domain analysis by sampling on a beat-by-beat basis (as opposed to a fixed frequency such as 5 Hz) and providing an "average frequency" based upon the average beat-to-beat R-R interval. Comparable treatment of laser Doppler and EKG data also may be achieved by resampling the beat-to-beat R-R data and the newly generated beat-to-beat laser Doppler data at 5 Hz to generate comparable pseudocontinuous signals.

The rate of changes on a beat-by-beat basis can then be assessed by looking at beat-to-beat differences, beat-to-beat percent change, normalized beat-to-beat differences as shown in FIG. 20. The advantage of any one of these embodiments of the invention is that it enables what was once a continuous wave form to be analyzed identically to that of the R wave.

The advantages of the means of analysis introduced herein are shown in FIG. 19, which shows that now data not only can be analyzed with comparable data manipulations but also that they can now be expressed on the same x- and y-axes (equivalent sampling frequencies and comparable magnitudes of power).

In addition to performing spectral-domain analysis over a fixed time interval (200 seconds), analysis can also be performed on moving average epochs (e.g., on wavelets). This would enable one to see the evolution of a response to a given challenge. For example, one can first perform spectral-domain analysis on a 200 second period that is entirely baseline and then progressively shift in 15 second epochs to the beginning of the given challenge and then progressively throughout the challenge. Using this method with an adaptation of a technique such as joint time-frequency analysis, one can more effectively identify the onset of a given response and also avoid the problem that may occur if the response is of relatively brief duration and thus attenuated by the lack of a response over a larger time period (e.g., a 30 second response would be markedly attenuated if it were incorporated within a 200 second window).

Whereas spectral-domain analysis of cardiovascular waveforms traditionally has been evaluated over an extended period of time, in many settings it would be of critical value to be able to assess the presence of parasympathetic activity in a very brief interval (in that offsetting responses over a longer period would tend to offset different signals and make them difficult to discern).

Figure 3A:
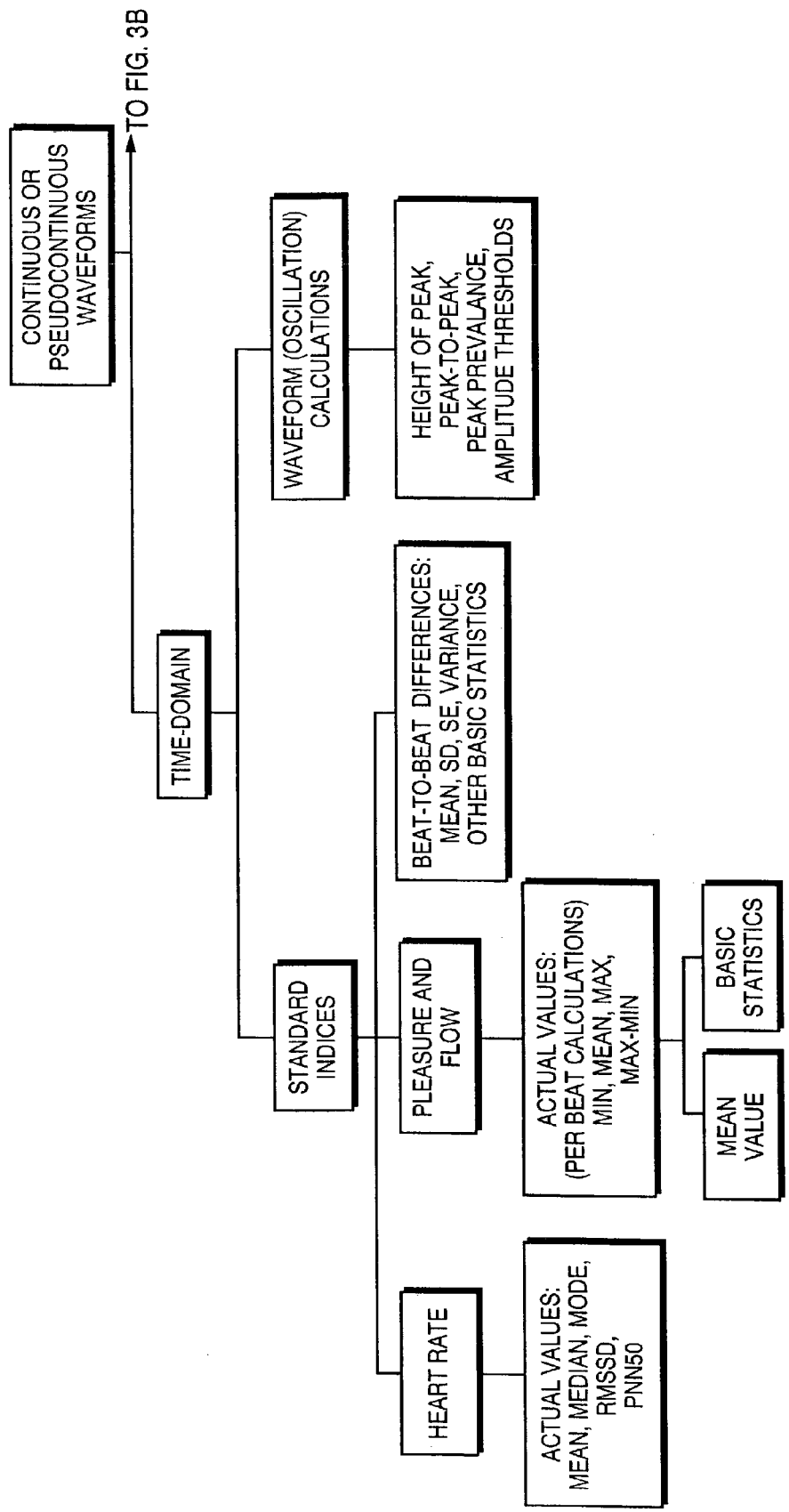
FIGS. 3A, 3B are a block diagram showing an overview of prior art methods for assessing heart rate (HR) variability, blood pressure (BP), and blood flow. This drawing presents various methods of assessing HR variability (ECG), flow variability (LDF), and BP variability (continuous BP monitor) according to the prior art.
Figure 3B:
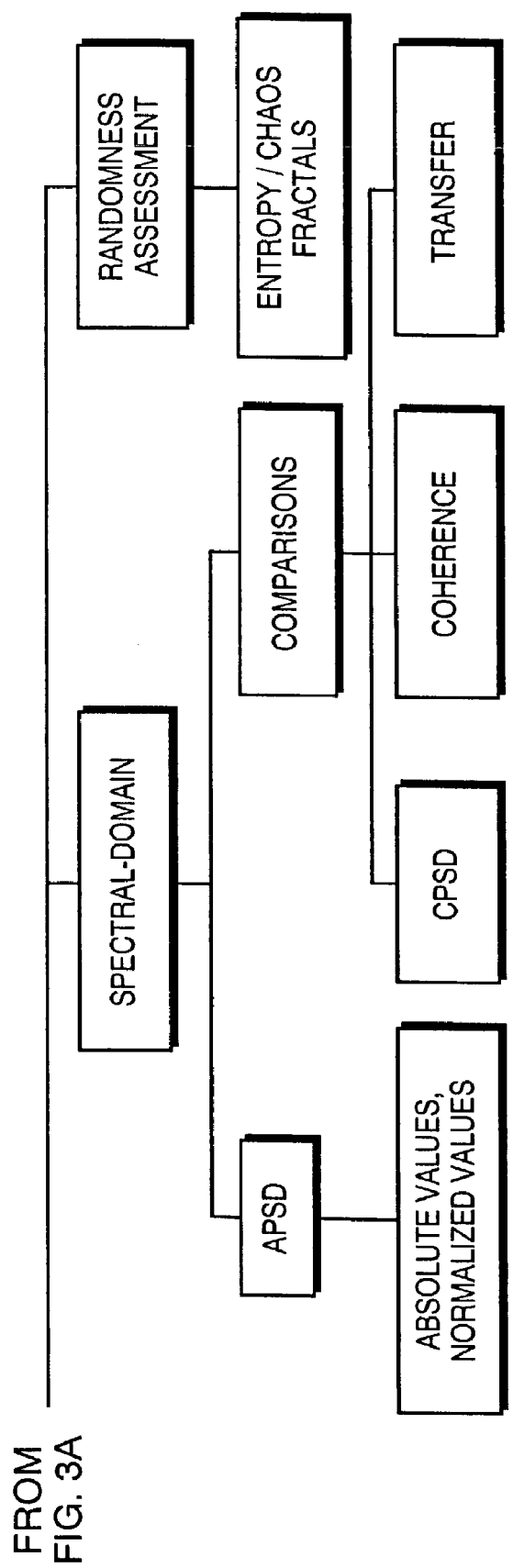

In order to further improve the delineation of spectral-domain changes at the desired frequency, we have introduced joint time-frequency analysis (JTFA) to enable documentation of dynamic changes in the harmonic content of cardiovascular waveforms. This technique previously has been limited to engineering applications such as sonography. Using a custom-written program in the Igor programming language, we have implemented a program for acquiring laser Doppler (and other continuous or pseudocontinuous or variable interval data treated as a waveform) signals (FIG. 3) and, in selected embodiments, normalized signals (FIG. 20). A preferred embodiment for input of parameters is provided in Table 1.

Table 1. Representative algorithm for JTFA of a subject receiving phenylephrine bolus.

| Parameter | Selection for Given Study |
|---|---|
| Window size (sec) | 82 |
| Frequency resolution | 0.0122 Hz |
| Degree of window overlap (sec) | 6 |
| Window type | Hann |
| Scaling | Linear |

-continued

| Parameter | Selection for Given Study |
|---|---|
| Type of display | Waterfall |
| Real-time or time-delayed | Real time |

JTFA is a preferred means for identifying the frequency and intensity of oscillatory activity that has been uniquely adapted to the cardiovascular waveforms described herein. A preferred embodiment of JTFA according to the present invention utilizes a window width of 82 seconds and a 6 second increment (see Table 1, above). The use of this method of "overlap" improves the ability to analyze a brief response; otherwise, the presence and/or intensity of a brief response may be lost/diluted if a standard window for spectral-domain analysis is employed to assess the oscillatory response to a transient stimulus. Thus, the introduction of JTFA enables one to avoid the "dilution" of power that can occur during a brief response such as that which may occur after rapid bolus injection of phenylephrine or an acute insult as may often occur during acute medical and surgical settings. For example, the application of joint time-frequency analysis enabled us to detect a change in the intermediate frequency range after a phenylephrine bolus that was 400% of that detected with traditional spectral domain analysis over a 2-minute interval (which was compromised by dilution of the peak response) (n=8 subjects). See FIG. 19 for an example of the type of data that is obtained.

We now explain the JTFA in detail. Depending on the spreadsheet program that is used, the inventive algorithm entails the following method steps for the calculation of the JTFA waveform (adopted from oxim to laser).

1. The waveform is converted to a numeric series by analog to digital conversion with sampling of the output at a rate determined by the user. The sampled waveform is collected into a digital buffer; e.g., 4096 points—82 seconds.
2. A windowing function is used on the data in the digital buffer (e.g. Hann)(FIG. 18). The windowing function is designed to minimize the effect of the finite range of the sample set.
3. A Fourier analysis is performed on the data set in the digital buffer with the aforementioned window. If one wishes to compensate for the potentially overwhelming signal strength for the heart rhythm in certain signals, then the data may be expanded in a logarithmic fashion.
4. The result is transferred to a display buffer which accepts new data from the given cardiovascular monitor(s) (e.g., laser Doppler) on a first-in, first-out basis. The amount of new data added (which determines the amount of overlap) may be determined by the user or synchronized with another source (e.g., respiratory rate; i.e., the amount of data associated with the time of one breath may be added to buffer).
5. Each new aliquot of data is then analyzed by the method outlined in steps 2 & 3.
6. The resulting data then can be plotted in a number of ways. A preferred embodiment is with Y axis—frequency & X axis—time, with intensity at a given frequency expressed by color or gray intensity. A number of different techniques can be used to display the results (false color, gray scale, "waterfall" or as a surface plot).

Thus, in the present invention, after determining one or more oscillatory signals from a subject, the characteristics of the signal are evaluated. Evaluation of the signal may involve the mathematical manipulation of the raw signal. In some preferred embodiments, the raw signal may be analyzed using a form of spectral-domain analysis. In some embodiments, the spectral-domain analysis may include one or more of the following: Fourier transformation, wavelet analysis, autopower spectral density (APSD) analysis or joint time-frequency analysis. In some embodiments, an APSD analysis of the signal may be prepared. When an APSD analysis is prepared, it may be desirable to determine the power in one or more frequency bins. Frequency bins are preferably small with respect to the range of the APSD and may be as small as allowed by the resolution based upon the window width used for the Fourier transformation and the sampling frequency of the technique used to acquire the signal. Frequency bins are preferably from about 0.005 Hz to about 0.02 Hz in width. In some embodiments, the power in one or more frequency bins in the region of the APSD analysis from about 0.12 Hz to about 0.20 Hz may be determined. In some embodiments, the power in a number of adjacent frequency bins which make up a frequency band may be determined. A frequency band may be narrow or wide relative to the width of the APSD and may comprise from about two to as many 20 or more frequency bins. Preferred frequency bands include, but are not limited to, the frequency band from about 0.10 Hz to about 0.20 Hz, the frequency band from about 0.12 Hz to about 0.18 Hz, the frequency band from about 0.12 Hz to about 0.20 Hz, and the frequency band from about 0.12 Hz to about 0.30 Hz.

In a preferred embodiment, the power in one or more frequency bins is determined before and after the subject is exposed to a physiologic challenge. This will allow the practitioner to see whether the subject is capable of properly responding to the challenge. The lack of an appropriate response may be used to diagnose one or more conditions of the subject. An improper response may be no response to the challenge when a response is seen in a normal subject, an already activated signal prior to the challenge when a normal subject would not be activated, a diminished or exaggerated response in all or a portion of the APSD analysis as compared to the response seen in a normal subject and/or reference signal.

In some embodiments, the power in one frequency bin is compared to the power in another frequency bin to determine a ratio. When the ratio is outside of a proper range, this information may be used to diagnose one or more pathological conditions. In some embodiments, the bins may be from an APSD analysis prepared from the same oscillatory signal. For example, an oscillatory signal may be determined and an APSD analysis prepared and the power in a frequency bin, for example the bin from 0.105 Hz to 0.110 Hz might be compared to the power in the frequency bin from 0.05 Hz to 0.06 Hz.

In other embodiments, the power in a frequency bin of an APSD analysis prepared from one oscillatory signal is compared to the power in a frequency bin of the same frequency in an APSD analysis prepared from a second oscillatory signal. The second oscillatory signal may be of the same type as the first, for example, both may be oscillatory signals from peripheral microvasculature determined with LDF analysis at two different sites of the subject. Alternatively, the oscillatory signals may be different. For example, the power in a frequency bin in an APSD analysis prepared from a LDF analysis of the peripheral microvasculature could be compared to the power in the corresponding frequency bin in an APSD analysis prepared from a HR variability analysis. Alternatively, the frequency bins may be of different frequency and the APSD analysis may be from the same or different oscillatory signal. The power in one or more bins or one or more bands may be compared.

In some embodiments, it may be desirable to compare the power in a selected frequency bin, for example the frequency bin having the maximum power, to the total and/or average power in one or more frequency bands or in the APSD as a whole. In such a comparison, it may be desirable to determine whether the average power in the selected frequency bin is greater or lesser than the average power in one or more frequency bands or in the APSD by a predetermined percentage. In some embodiments, it may be desirable to compare the power in a selected frequency bin, for example the frequency bin containing the maximum power, to another selected frequency bin, for example the frequency bin containing the minimum power.

When APSD analysis of two or more different types of oscillatory signal are compared, it may be desirable to normalize the different results. This will result in a common set of units for each signal and provide a means of assessing different the results of two or more different types of analysis. Normalization may be achieved by any of the following methods: normalizing the data resampled at 5 Hz to the mean or median value of the given parameter for the given study segment; dividing the power in the APSD by the mean; dividing each raw data point by the mean value of the given parameter for the given study segment; or time-domain analysis modified by determining beat-to-beat % change. As shown in FIGS. 12A-D and 13A-D, this can then be used for graphic display or for determination of the $APSD_{\%change}$. Other means of normalizing time-domain data include dividing the size of oscillations (peak-to-trough) at the desired frequency by the mean or median, or dividing the time-domain parameter, such as SD or rmSSD, by the median or mean.

In some embodiments, an oscillatory signal from a subject may be compared to a reference oscillatory signal. In general a reference oscillatory signal can be any oscillatory signal to which another oscillatory signal is compared. A reference oscillatory signal may be a signal from the same subject, a different subject, an average signal from a plurality of subjects or a theoretically derived signal. In some embodiments, the reference signal may be obtained from the same subject at a different time. In some preferred embodiments of this type, a reference signal may be determined from the subject before or after exposing the subject to a physiologic challenge. It is not critical to the practice of the invention whether the signal before the challenge is termed the reference signal or whether the signal after the challenge is termed the reference signal. In some embodiments of the present invention, a reference signal may be an oscillatory activity obtained from the subject at a first site that is compared to an oscillatory activity obtained from a subject at a second site. The reference signal may be obtained before, concurrently with or after the signal to which it is compared, although in preferred applications comparisons between different sites are obtained simultaneously. The reference signal may be determined from the same or different type of oscillatory activity as the signal to which it is compared. When a reference signal is determined from a different type of oscillatory activity than the signal to which it is compared, it may be desirable to normalize the signals. For example, if a reference signal determined from HR variability or BP were to be compared to a signal determined from an oscillatory activity in the peripheral microvasculature according to the present invention, it may be desirable to normalize the two signals. Likewise, if a reference signal determined from an oscillatory activity in the peripheral microvasculature according to the present invention were to be compared to a signal determined from HR variability or BP, it may be desirable to normalize the two signals.

In one aspect, the present invention provides a method of assessing a condition of a subject's cholinergic oscillatory control of the microvasculature ($COC_{micvasc}$) and of his/her parasympathetic nervous system by exposing the subject to a physiologic challenge, measuring oscillatory activity of a microcirculatory blood vessel (arteriole and/or capillary) and, in the preferred embodiment, a plurality of blood vessels disposed in a peripheral region of the subject's vascular system wherein the measuring step is performed by: 1) observing the vessel(s) for oscillatory activity in the desired frequency range (e.g., approximately 0.12-0.18 Hz) with a technique such as videomicroscopy; or 2) probing the plurality of blood vessels with an interrogation signal, receiving a reflected signal from the plurality of blood vessels, and evaluating characteristics of the reflected signal in the approximate 0.12 to 0.18 Hz frequency band with a technique such as LDF. The sought-for change in the LDF signal may be generated by oscillations of individual vessels or by coordination of oscillations of the multiple vessels under the LDF probe. The 0.12-0.18 Hz range is preferred but frequencies >0.18 Hz may be included so long as overlap with respiratory rate (e.g. 0.20 Hz during breathing at 12 breaths/min) is corrected for or avoided; frequencies <0.12 Hz may be included so long as the sympathetic contribution is excluded (e.g. with administration of a sympatholytic drug).

To permit optimal identification of $COC_{micvasc}$, one can fix the respiratory rate at a frequency beyond the typical range for $COC_{micvasc}$. In individuals on a ventilator, this can be done by setting the ventilator setting to $\geq 0.2$ Hz (1 breath/5 seconds). For patients breathing on their own, their rate can be established by having them breathe in response to a metronome at $\geq 0.2$ Hz. As shown by the data herein, the APSD clearly distinguishes between the typical $COC_{micvasc}$ frequency (between 0.12 and 0.18 Hz) and the respiratory frequency. When there is the potential for overlap (most commonly when breathing occurs at a slightly slower rate and thus is within the IF band), it is important to document the precise frequency of respiration so that one can determine its impact or potential impact on a given signal. There would be a high degree of coherence with R-R variability but a low degree of coherence with flux of the forehead microvasculature. When one is assessing the effect of a pharmacologic challenge such as phenylephrine, it would be important to document that respiratory frequency and approximate respiratory power remain the same, such that any change during the phenylephrine challenge would not be artificially induced by a change in respiration.

In a related aspect, the present invention provides a method of assessing a condition of a subject's parasympathetic nervous system by comparing the cholinergically induced changes to the baseline state. In other aspects, the present invention provides a method of assessing $COC_{micvasc}$ and a condition of a subject's parasympathetic nervous system while the subject simply is at rest.

In one aspect, the present invention provides a method of assessing a condition of a subject's parasympathetic nervous system by measuring oscillatory activity of one or more blood vessels disposed in a peripheral region of the subject's vascular system while the subject is at rest, evaluating characteristics of the measured oscillatory activity in the 0.12 to 0.18 Hz frequency band, comparing the measured oscillatory activity to a reference oscillatory activity such as respiratory oscillations, HR variability or BP oscillations and assessing the condition of $COC_{micvasc}$ and of the parasympathetic nervous system of the subject based upon similarities or differences in the measured oscillatory activity and the reference oscillatory activity.

In addition to assessing relative effects of challenges on different indices such as $COC_{micvasc}$ and $COC_{HR}$, the invention may also be used to assess different effects of therapies on disorders such as neuropathies and hypertension. In one aspect, the present invention provides a method of diagnosing an autonomic neuropathy in a subject by measuring oscillatory activity of a vessel or plurality of blood vessels disposed in a peripheral region of the subject's vascular system, determining a power spectrum of the oscillatory signal and determining power in a band from 0.12 Hz to 0.18 Hz of the power spectrum, wherein a reduction of the amount of 0.12-0.18 Hz oscillatory activity, which may be measured as power in the band from 0.12 Hz to 0.18 Hz is indicative of an autonomic neuropathy which compromises $COC_{micvasc}$. In some embodiments, the autonomic neuropathy is diabetic neuropathy. In some embodiments, measuring may entail probing a plurality of blood vessels with an interrogation signal and receiving a reflected signal from the plurality of blood vessels. In some embodiments, the method may further comprise exposing the subject to a physiologic challenge.

In some embodiments, the present invention provides a method of diagnosing hypertension or a predisposition to hypertension and/or an altered pre-hypertensive state in a subject by measuring oscillatory activity in a vessel or of a plurality of blood vessels disposed in a peripheral region of the subject's vascular system, determining a power spectrum of the oscillatory signal and determining power in a band or within a region of the band from 0.12 Hz to 0.18 Hz of the power spectrum, wherein the amount of power in the band from 0.12 Hz to 0.18 Hz is indicative of hypertension, a predisposition to hypertension and/or an altered pre-hypertensive state. In some embodiments, measuring may entail probing a plurality of blood vessels with an interrogation signal and receiving a reflected signal from the plurality of blood vessels. In some embodiments, the method may further comprise exposing the subject to a physiologic challenge.

In some embodiments, the present invention provides a method of assessing a condition of a subject's parasympathetic nervous system by measuring oscillatory activity of one or more blood vessels disposed in a first peripheral region of the subject's vascular system, determining a power spectrum of the oscillatory activity and evaluating characteristics of the reflected signal in the 0.12 to 0.18 Hz frequency band, measuring oscillatory activity of one or more blood vessels disposed in a second peripheral region of the subject's vascular system, determining a power spectrum of the oscillatory activity and evaluating characteristics of the reflected signal in the 0.12 to 0.18 Hz frequency band, comparing the characteristics of the power spectrum obtained from the first peripheral region with the characteristics of the power spectrum obtained from the second peripheral region, wherein similarities or differences in the characteristics of the signals indicate the presence, absence or extent of the condition. In some embodiments, measuring may entail probing a plurality of blood vessels with an interrogation signal and receiving a reflected signal from the plurality of blood vessels. In some embodiments, the method may further comprise exposing the subject to a physiologic challenge.

Given the correlation between the character of the activity of the autonomic nervous system and the prognosis in various pathological states, there exists a need in the art to facilitate the characterization of the activity of the autonomic nervous system in order to facilitate the diagnosis of pathological conditions. By determining that the activity of cholinergic innervation (i.e., of the parasympathetic nervous system) may be characterized in the peripheral microvasculature, the present invention has met this and other needs. Use of the present invention will improve the ability of medical practitioners to characterize, monitor, and treat the autonomic dysfunction and end-organ injury that characterizes disorders such as hypertension, regional ischemia, and diabetes.

In some embodiments, the oscillatory power at the desired frequency range can be assessed with time-domain measurements of the amplitude and incidence of oscillations at said frequency. Such assessments may be more amenable to real-time monitoring of oscillatory activity than generation of the APSD. The frequency of such oscillations may be determined by the APSD (as described above) or by direct assessment of the successive oscillations in the real-time waveform.

Data Normalization Techniques

Equations (6) and (7) below represent two prior art time-domain indices:

$$\text{Standard Deviation} = SD = \sqrt{\Sigma(x-\bar{x})^2/(N-1)} \quad (6)$$

(where x=individual value, $\bar{x}$=mean value, N=# of values)

$$\text{Root Mean Square of Successive Differences} = rmssd = \sqrt{[\Sigma((x+1)-x)^2]/N} \quad (7)$$

(where x=individual value, x+1=next individual value, N=total # of individual values)

Several inventive modifications of these standard indices based upon the normalization procedure discussed in connection with FIGS. 11 and 12 are shown in equations (8) and (9) below. They are designed to enable comparisons of different signals and different times, as well as different laser Doppler sites with different numbers of vessels.

$$\text{SD of pre-normalized data} = \sqrt{\Sigma(x\text{norm}-\bar{x}\text{norm})^2/(N-1)} \quad (8)$$

(where $x_{norm}$=normalized value of individual data points as determined by the normalization methods discussed in connection with FIG. 11 or 12; $\bar{x}_{norm}$=mean of the values that are normalized by the method utilized for $x_{norm}$; N=# of values)

$$\text{rmssd of prenormalized date} = \sqrt{[\Sigma((x+1)\text{norm}-x\text{norm})^2]/N} \quad (9)$$

(where $x_{norm}$=normalized value of individual data points as determined by the normalization methods illustrated in FIG. 11 or FIG. 13; $(x+1)_{norm}$=normalized value of next individual data point; N=total # of values)

The present invention also includes modification of the standard indices by division by the median or mean value for the given parameter during the given assessment phase as shown by equations (10) and (11) below:

$$\text{Normalization after time domain} = SD/\text{median} = \sqrt{\Sigma(x-\bar{x})^2/(N-1)}/\text{median} \quad (10)$$

(where x=individual value, x̄=mean value, N=# of values)

$$\text{rmssd/median} = (\sqrt{[\Sigma((x+1)-x)^2]/N})/\text{median} \quad (11)$$

(where x=individual value, x+1=next individual value, N=total # of individual values)

Normalization of time-domain indices by these and other techniques facilitates interphase and interparameter comparisons as set forth in the present invention. The indices may stand alone as new formulae for assessment of oscillatory activity of biologic waveforms and, more specifically, may be assessed in the context of desired oscillatory frequencies (as demonstrated in FIG. 18). A still further inventive modification of a standard time-domain indice (contrasted with the prior art PNN50 indice (i.e., percentage of R-R intervals that differed from the preceding R-R interval by at least 50 msec—equation (12)) is the PBB5% indice (i.e., percentage of beat-to-beat changes that are at least 5%) shown in equation (13) below:

$$\frac{(\text{\# of R-R intervals that differed from preceding R-R interval by} > 50 \text{ msec}) \times 100}{(\text{Total \# of R-R intervals})} \quad (12)$$

$$PBB5\% = \frac{(\text{\# of beat-to-beat \% changes} > 5\%) \times 100}{(\text{Total \# of beat-to-beat \% changes})} \quad (13)$$

(where BB = beat-to-beat difference for the given index (e.g. R-R or flux))

In the PBB5% index, the beat-to-beat % change was used to modify the pNN50, a traditional index for quantifying HR variability according to the number of times that an R-R interval differed from the preceding R-R interval by more than 50 msec. Instead of relying upon the absolute difference (msec) between beats, this new method applied a relative difference (beat-to-beat % change) so as to permit application of the index to flux data and thereby allow comparisons between flux and HR with a comparable cutoff (e.g., pBB5%). Although any one of a number of cutoffs could be used, the 5% cutoff is a preferred embodiment because this represents 50 msec when the R-R is 1000 msec. The pBB5% permits a comparable determination of flux variability that otherwise would not be obtainable with the traditional pNN50.

A still further modification of a normalized index achieved by multiplying the index by the relative oscillatory power at a given frequency (i.e., % of overall variability assessed by SD/median that is attributable to oscillations at 0.14 Hz) is shown by equation (14) below:

$$(\text{SD/median}) \times (\text{power at } 0.14 \text{ Hz/total power}) \quad (14)$$

Moreover, the change in variability attributable to power at 0.14 Hz may be calculated in accordance with equation 15 below

[(SD/median during PHENYL)×(power at 0.14 Hz during PHENYL)]/[(SD/median during BASE)× (power at 0.14 Hz during BASE)]  (15)

This modification provides a method for determining the % of overall variability that is attributable to oscillations at the desired frequency. It also serves as a way of determining if changes in overall variability are attributable to specific oscillatory responses to a given challenge. The frequency may be determined from APSD or by inspection of a graphic display. Note, if it is clear that variability is solely due to a specific frequency or clearly not due to a specific frequency, then the inventive time-domain indices described above can stand alone and the above steps may not be necessary (i.e., it may not be necessary to identify a given oscillatory frequency or correct for the relative amount of oscillatory power at a given frequency.)

Any reference in the specification to "one embodiment" or "an embodiment" means that a particular feature, structure, or characteristic described in connection with the embodiment is included in at least one embodiment of the invention. Each of the features, characteristics or structures thus referred to may be present in any or all of the embodiments of the present invention independently of the presence or absence of any other features, characteristics or structures.

Although the present invention has been described in detail above, those skilled in the art will appreciate that various modifications may be made without departing from the spirit of the invention. All articles, patents and other materials referred to above are specifically incorporated herein by reference.

We claim:

1. A method of selectively identifying frequency and power of cholinergic oscillatory activity in microvasculature of a human comprising:
   a). measuring the frequency and power of the oscillatory activity in the microvasculature of the human at a frequency of from about 0.12 Hz to about 0.18 Hz; and
   b). distinguishing the measured activity obtained in step a) from the sympathetic oscillatory activity and the proximally generated parasympathetic oscillatory activity, thereby selectively identifying the frequency and power of the cholinergic oscillatory activity.

2. The method of claim 1, wherein distinguishing the cholinergic oscillatory activity from the proximally generated parasympathetic activity comprises controlling effects of respiration by setting the human's respiratory rate to 0.20 Hz or greater.

3. The method of claim 2, wherein the effects of respiration are controlled by having the human breathe voluntarily at a rate of 0.20 Hz or greater.

4. The method of claim 1, wherein the measured activity is distinguished from frequencies less than about 0.12 Hz, and from frequencies greater than about 0.18 Hz, by utilizing a method selected from the group consisting of frequency subtraction, signal filtering, analyzing absolute frequency contributions, analyzing relative frequency contributions, and determining proportional activities of the frequencies.

5. The method of claim 1, wherein the measuring comprises monitoring a plurality of vessels of the microvasculature.

6. The method of claim 1, wherein the measuring comprises monitoring a plurality of blood vessels in the distal microvasculature.

7. A method of assessing cholinergic oscillatory activity of a subject comprising:
   a). measuring the frequency and power of the oscillatory activity of a cardiovascular signal in the microvasculature of the subject at a frequency from about 0.12 Hz to about 0.18 Hz; and
   b). distinguishing the measured activity obtained in step a) from the sympathetic oscillatory activity and the proximally generated parasympathetic oscillatory activity, thereby selectively identifying the frequency and power of the cholinergic oscillatory activity in the microvasculature, and c). assessing the condition of the subject, wherein the cholinergic oscillatory activity is indicative of an autonomic dysfunction, an autonomic neuropathy, a prehypertensive state, a hypertensive state, a decrease in parasympathetic activity, and diabetes.

8. The method of claim 7, wherein the cardiovascular signal is detected in a vessel or a plurality of vessels.

9. The method of claim 7, wherein the measurement is accomplished using a laser Doppler flowmeter.

10. The method of claim 7, wherein the data are further analyzed by determining the power of the frequencies in individual bins and/or individual bands.

11. The method of claim 7, further comprising normalizing the oscillatory activity data by: measuring the oscillatory activity at different times, measuring the oscillatory activity at different sites in the peripheral vasculature, or measuring the oscillatory activity with different devices.

12. The method of claim 11, wherein the data are normalized to a mean value obtained for a given period of measurement.

13. The method of claim 11, wherein the data are normalized to a median value obtained for a given period of measurement.

14. The method of claim 11, further comprising performing spectral-domain analysis of the normalized data.

15. The method of claim 7, wherein the oscillatory activity data are converted to discrete variable time interval data so as to facilitate comparisons to R-R intervals and EKG measurements.

16. The method of claim 7, further comprising performing time-domain analysis of the data.

17. The method of claim 16, further comprising determining indices such as maximum, minimum, and max-min of individual signals on a beat-to-beat basis.

18. The method of claim 17, further comprising determining the beat-to-beat percent change.

19. The method of claim 18, further comprising determining the percentage of beat-to-beat changes beyond an established cutoff.

20. The method of claim 19, wherein the established cutoff is 5% (PBB5%) or 10% (PBB 10%).

21. The method of claim 16, further comprising mathematically manipulating the data to determine indices for comparison.

22. The method of claim 21, further comprising determining the normalization of time-domain indices of variability of waveforms by dividing an index by the mean value of the signal during a specific study interval.

23. The method of claim 22, further comprising determining the normalization of time-domain indices of variability of waveforms by dividing an index by the median value of the signal during a specific study interval.

24. The method of claim 7, wherein the method utilizes graphic time-domain displays.

25. The method of claim 7, wherein the measuring step is accomplished from an event selected from the group consisting of baseline, during drug therapy, during physiological challenges, during psychological challenges, and various stages of a disease.

26. The method of claim 7, wherein the data are analyzed using joint time-frequency analysis.

27. The method of claim 26, wherein the data are measured using a laser Doppler flowmeter.

28. The method of claim 7, wherein the subject is exposed to a pharmacologic challenge.

* * * * *